United States Patent
Odorico et al.

(10) Patent No.: US 9,540,613 B2
(45) Date of Patent: Jan. 10, 2017

(54) METHODS FOR PRODUCING INSULIN-SECRETING BETA CELLS FROM HUMAN PLURIPOTENT STEM CELLS

(71) Applicant: Wisconsin Alumni Research Foundation, Madison, WI (US)

(72) Inventors: Jon Scott Odorico, Fitchburg, WI (US); Xiaofang Xu, Madison, WI (US); Melisa Wittkowske, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/263,123

(22) Filed: Apr. 28, 2014

(65) Prior Publication Data

US 2014/0329315 A1 Nov. 6, 2014

Related U.S. Application Data

(60) Provisional application No. 61/817,061, filed on Apr. 29, 2013.

(51) Int. Cl.
| | | |
|---|---|---|
| C12N 5/00 | (2006.01) | |
| C12N 5/071 | (2010.01) | |
| C12N 5/074 | (2010.01) | |

(52) U.S. Cl.
CPC ........... *C12N 5/0676* (2013.01); *C12N 5/0607* (2013.01); *C12N 2500/25* (2013.01); *C12N 2500/30* (2013.01); *C12N 2501/115* (2013.01); *C12N 2501/117* (2013.01); *C12N 2501/119* (2013.01); *C12N 2501/155* (2013.01); *C12N 2501/16* (2013.01); *C12N 2501/30* (2013.01); *C12N 2501/33* (2013.01); *C12N 2501/335* (2013.01); *C12N 2501/385* (2013.01); *C12N 2501/998* (2013.01); *C12N 2506/02* (2013.01); *C12N 2506/03* (2013.01); *C12N 2506/45* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 8,247,229 B2 | 8/2012 | Odorico | |
| 8,685,730 B2* | 4/2014 | Odorico et al. | .............. 435/377 |
| 8,741,643 B2* | 6/2014 | Rezania et al. | .............. 435/377 |
| 2010/0081200 A1* | 4/2010 | Rajala et al. | ................ 435/377 |
| 2012/0264209 A1 | 10/2012 | Odorico | |

FOREIGN PATENT DOCUMENTS

WO 2012170853 A1 12/2012

OTHER PUBLICATIONS

D'Amour et al. Nat Biotech 2006;24:1392-1401.*
Brewer et al. J Neurosci Res 1993;35: 567-76.*
Wang et al. Biochem Biophys Res Comm 2005;330:934-42.*
Xu, R., et al., "BMP4 initiates human embryonic stem cell differentiation to trophoblast" Nature Biotechnology, vol. 20; 1261-1264 (2002).
Chan, E.M., Ratanasirintrawoot, S., et al. "Live cell imaging distinguishes bona fide human iPS cells from partially reprogrammed cells" Nat. Biotech. vol. 27, No. 11; 1033-1037 (2009).
Yu, J., Vodyanik, M.A., et al. "Induced pluripotent stem cell lines derived from human somatic cells." Science, vol. 318, No. 5858; 1917-1920 (2007).

* cited by examiner

*Primary Examiner* — Janice Li
(74) *Attorney, Agent, or Firm* — Quarles & Brady, LLP

(57) ABSTRACT

A method of culturing human pluripotent stem cells to produce pancreatic lineage, the method comprising the steps of (a) culturing the stem cells in the presence of a chemically defined medium comprising an effective amount of FGF, Activin A, and BMP; (b) culturing the cells from step (a) in the presence of a chemically defined medium comprising an effective amount of insulin, transferrin, and selenium (ITS), and FGF; (c) culturing the cells from step (b) in the presence of a chemically defined medium comprising an effective amount of insulin, transferrin, and selenium (ITS), and Noggin-Nicotinamide-Retinoic acid; and (d) culturing the cells from step (c) in the presence of a serum free chemically defined medium (ITSFINE and Noggin) comprising an effective amount of ITS, FGF7, islet neogenesis associated peptide (INGAP), nicotinamide, and Exendin-4, wherein pancreatic lineage cells are produced, wherein the pancreatic lineage cells are insulin$^+$ cells.

21 Claims, 26 Drawing Sheets
(26 of 26 Drawing Sheet(s) Filed in Color)

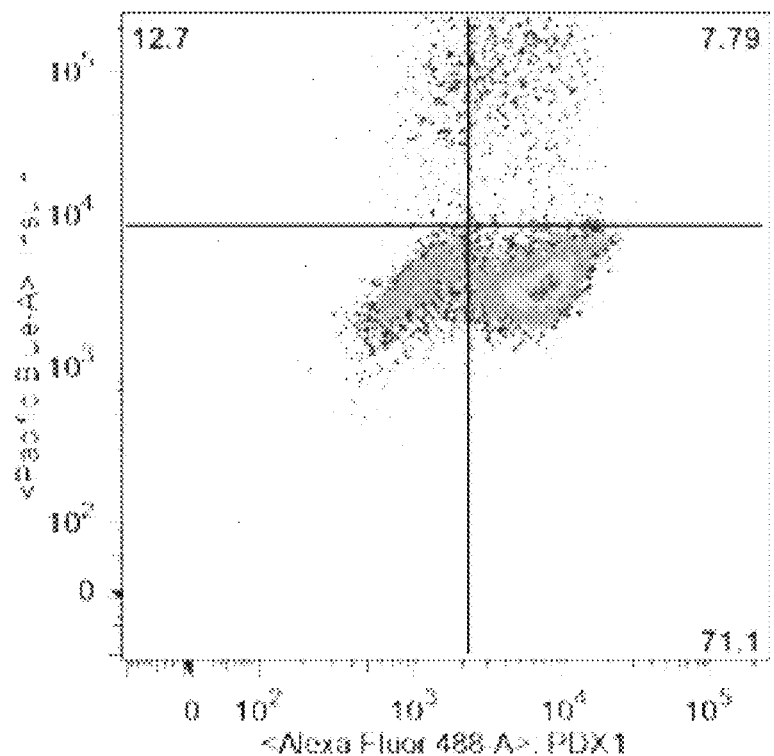
Figure 8 - Continued

Alterations at Stage 3 and 4 Significantly Alter Protein Expression

Stage 4: without Noggin

PDX1 / Insulin

Stage 4: with Noggin

PDX1 / Insulin / DAPI

METHODS FOR PRODUCING INSULIN-SECRETING BETA CELLS FROM HUMAN PLURIPOTENT STEM CELLS

CROSS-REFERENCE TO RELATED APPLICATIONS

This application claims the benefit of U.S. Provisional Patent Application Ser. No. 61/817,061, filed on Apr. 29, 2013, which is incorporated by reference in its entirety for all purposes.

STATEMENT REGARDING FEDERALLY SPONSORED RESEARCH OR DEVELOPMENT

N/A

BACKGROUND OF THE INVENTION

Type I diabetes is an autoimmune disease of humans caused by destruction of pancreatic islet β cells. Transplantations of whole pancreas or isolated islet cells are effective treatments for Type I diabetes to restore insulin independence, when combined with immunosuppressive therapy. Successful transplantation of isolated islets from human cadaver donors is a proof-in-principle that a cell-based therapy for human diabetes can be successful. However, the lack of available and variable quality of organs and islet cells has restricted this therapy to very few patients. The amount of islet cells which can be harvested from human cadavers is extremely limited. Therefore, technologies capable of producing significant quantities of cells of the pancreatic lineage are highly desirable.

Stem cells are cells that are capable of differentiating into many cell types. Embryonic stem cells are derived from embryos and are potentially capable of differentiation into all of the differentiated cell types of a mature body. Certain types of stem cells are "pluripotent," which refers to their capability of differentiating into many cell types. One type of pluripotent stem cell is the human embryonic stem cell (hESC), which is derived from a human embryonic source. Human embryonic stem cells are capable of indefinite proliferation in culture, and therefore, are an invaluable resource for supplying cells and tissues to repair failing or defective human tissues in vivo.

Similarly, induced pluripotent stem (iPS) cells, which may be derived from non-embryonic sources, can proliferate without limit and differentiate into each of the three embryonic germ layers. It is understood that iPS cells behave in culture essentially the same as ESCs. Human iPS cells and ES cells express one or more pluripotent cell-specific markers, such as Oct-4, SSEA-3, SSEA-4, Tra 1-60, Tra 1-81, and Nanog (Yu, et al. *Science*, Vol. 318. No. 5858, pp. 1917-1920 (2007)). Also, recent findings of Chan, suggest that expression of Tra 1-60, DNMT3B, and REX1 can be used to positively identify fully reprogrammed human iPS cells, whereas alkaline phosphatase, SSEA-4, GDF3, hTERT, and NANOG are insufficient as markers of fully reprogrammed human iPS cells. (Chan, et al., *Nat. Biotech.* 27:1033-1037 (2009)). Subsequent references herein to hESCs and the like are intended to apply with equal force to iPS cells.

One of most significant features of hESCs is their ability to self-renew: hESCs can proliferate into multiple progeny, each having the full potential of its immediate ancestor. In other words, the progeny are pluripotent and have all the developmental and proliferative capacity of the parental cell. Self-renewal appears mutually exclusive with differentiation, as only undifferentiated hESCs are capable of indefinite self-renewal. Upon commitment toward any cell lineage, the attribute of perpetual self-renewal is lost. Therefore, to avoid uncontrolled differentiation of hESCs, care must be taken to maintain the cells in an undifferentiated state.

Previously, we have discovered several techniques for culturing hESCs and iPS cells into cells of the pancreatic lineage, such as those disclosed in U.S. Pat. No. 8,247,229 and U.S. Patent Application Publication No. 2012/0264209. It has been shown in these two disclosures that reproducible culture methods utilizing defined components can promote islet cell differentiation from human pluripotent stem cells. Specifically, U.S. Pat. No. 8,247,229 describes a 3-stage protocol to differentiate hESCs and hiPSCs into cells that adopt pancreatic fates. This protocol is based on BMP4 treatment of undifferentiated cells during Stage 1, formation of embryoid bodies (EB) during Stage 2, and further differentiation during Stage 3. While the resulting cells were PDX1$^+$Insulin$^+$, the amount of insulin produced is relatively limited. Also, the culture conditions of the protocol were not defined as serum and conditioned media were used. On the basis of this protocol, U.S. Patent Application Publication No. 2012/0264209 further improves the stability of the pancreatic lineage by using TransWell™, typically during the last stage to allow maintenance of a PDX1$^+$Insulin$^-$ putative progenitor population in culture and in which the cells are stable in culture without further differentiation for at least 70 days. To promote cell-cell contact and create an islet-like environment, EBs are embedded in Matrigel™ and treated with a cocktail of insulin-transferrin-selenium-FGF7-INGAP-nicotinimide-Exendin-4 (ITSFINE), producing distinct sphere-structured cell clusters ("pancreas-spheres"). The cells in the pancreas-spheres are almost entirely PDX1$^+$, SOX9$^+$, FOXA2$^+$, HNF1β$^+$, and HNF6$^+$ markers characteristic of human pancreatic epithelium. A portion of the cells also express PTF1A, CPA, NGN3, and NKX6.1, which is characteristic of multi-potent pancreatic progenitor cells. Furthermore, some pancreas-spheres exhibit budding/branching structures, reminiscent of normal pancreatic morphological development. Culturing pancreas spheres in medium containing Nicotinamide leads to a significant increase at the end of the culture period in the number of cells that co-stain with PDX1 and insulin/C-peptide, characteristic of normal adult β cells. However the percentage of insulin-positive cells is low, and secretion of human C-peptide into the medium is also low.

U.S. Pat. No. 8,685,730 also discloses a simplified protocol, in which Matrigel™ is used at Stage 2. By using Matrigel™ at this stage, the transition from APS/DE to posterior foregut can be shortened by 7 days. From the end of Stage 2, the simplified protocol follows the same stages of the standard protocol, i.e., culturing cells from Stage 2 for at least another two weeks. While the simplified protocol represents a relatively shorter period of time for culturing, the protocol only produced pancreatic progenitors (PDX1$^+$Insulin$^-$). There is no insulin produced by the cells produced by that protocol.

Although these protocols are highly reproducible, the relatively long culture period amplifies the cost of media and personnel time, and impedes efficient testing of additional growth factors that may advance the protocol. In addition, the longer culture period can promote undesirable deviation from specific directed lineage progression and variability in the results. As such, a shortened and improved protocol is desired. Fortunately, advances in our understanding of extrinsic signaling events controlling the formation of definitive endoderm and regional specification of the pancreas are leading to new methodologies for directed differentiation of stem cells into cells of the pancreatic lineage. Also, subtle differences in media growth factor concentrations, combinations, timing and/or sequence of growth factor introduction, and length of incubation with particular growth factors may induce pluripotent stem cells to differentiate into many different cell lineages. Moreover, the types and concentrations of supporting extracellular matrix components may further affect the differentiation of pluripotent stem cells.

SUMMARY OF THE INVENTION

The present invention relates to methods of culturing human pluripotent stem cells to produce posterior foregut cells and/or pancreatic lineage cells, and uses thereof.

In its first aspect, the present invention provides methods of culturing human pluripotent stem cells to produce posterior foregut cells, comprising the steps of:
(a) culturing human pluripotent stem cells for about 3 days in the presence of a chemically defined medium under conditions that induce formation of mesendoderm/primitive streak and definitive endoderm cells, wherein the medium comprises an effective amount of;
  i) fibroblast growth factor (FGF),
  ii) Activin A, and
  iii) bone morphogenetic protein (BMP);
(b) culturing the cells from step (a) for about 3 days in the presence of a chemically defined medium comprising an effective amount of;
  i) insulin, transferrin, and selenium (ITS), and
  ii) fibroblast growth factor (FGF); and
(c) culturing the cells from step (b) for about 4 days in the presence of a chemically defined medium comprising an effective amount of;
  i) insulin, transferrin, and selenium (ITS), and
  ii) Noggin-Nicotinamide-Retinoic acid (NNR),
wherein the posterior foregut cells are produced.

In its second aspect, the present invention provides methods of culturing posterior foregut endoderm cells to produce cells of the pancreatic lineage, the method comprising the step of:
(a) culturing the posterior foregut endoderm cells for about 7 days in the presence of a serum free chemically defined medium (ITSFINE) comprising an effective amount of;
  i) insulin, transferrin, selenium, FGF7, islet neogenesis associated peptide (INGAP), nicotinamide, and exendin-4, and
  ii) Noggin,
wherein pancreatic lineage cells are produced, wherein the pancreatic lineage cells are insulin$^+$ cells.

In its third aspect, the present invention provides methods of culturing human pluripotent stem cells to produce cells of the pancreatic lineage, the method comprising the steps of:
(a) culturing human pluripotent stem cells for about 3 days in the presence of a chemically defined medium under conditions that induce formation of mesendoderm/primitive streak and definitive endoderm cells, wherein the medium comprises an effective amount of;
  i) fibroblast growth factor (FGF),
  ii) Activin A, and
  iii) bone morphogenetic protein (BMP);
(b) culturing the cells from step (a) for about 3 days in the presence of a chemically defined medium comprising an effective amount of;
  i) insulin, transferrin, and selenium (ITS), and
  ii) fibroblast growth factor (FGF);
(c) culturing the cells from step (b) for about 4 days in the presence of a chemically defined medium under conditions that induce formation of posterior foregut cells, wherein the medium comprises an effective amount of;
  i) insulin, transferrin, and selenium (ITS), and
  ii) Noggin-Nicotinamide-Retinoic acid (NNR); and
(d) culturing the cells from step (c) for about 7 days in the presence of a serum free chemically defined medium (ITSFINE) comprising an effective amount of;
  i) insulin, transferrin, selenium, FGF7, islet neogenesis associated peptide (INGAP), nicotinamide, and exendin-4, and
  ii) Noggin,
wherein pancreatic lineage cells are produced, wherein the pancreatic lineage cells are insulin$^+$ cells.

In its fourth aspect, the present invention provides cell populations comprising posterior foregut cells prepared by methods described above.

In its fifth aspect, the present invention provides cell population comprising pancreatic lineage cells is prepared by methods described above.

In its sixth aspect, the present invention provides methods of using the cell population prepared by using the cell culture methods described above for drug screening, comprising the step of (a) exposing the cells to a drug; and (b) observing whether the drug promotes progenitor cell survival or proliferation or beta cell regeneration.

In its seventh aspect, the present invention provides methods of using the cell population prepared by using the cell culture methods described above for a cell/tissue transplant, comprising the step of transplanting the progenitor cells into a mammalian patient.

BRIEF DESCRIPTION OF THE DRAWINGS

This patent application file contains at least one drawing executed in color. Copies of this patent or patent application publication with color drawings will be provided by the Office upon request and payment of the necessary fee.

DETAILED DESCRIPTION OF THE INVENTION

Figure 1:
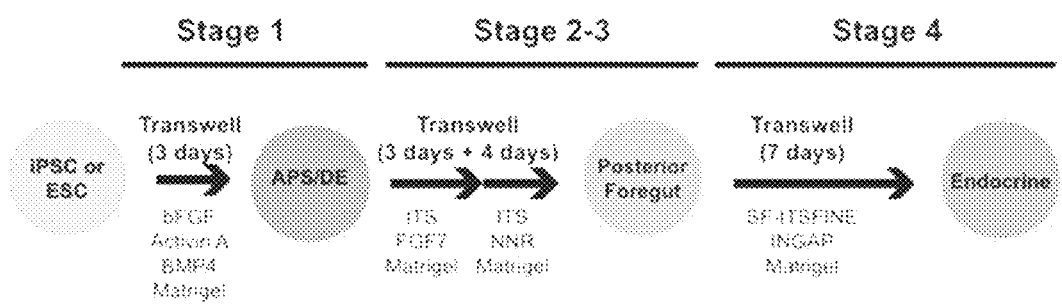
FIG. 1 is a flowchart illustrating the general protocol of preparing pancreatic lineage cells from human embryonic stem cells and/or human induced pluripotent stem cells.

In a broad aspect, the present invention provides a novel four-stage protocol to differentiate hESCs and human iPSCs into cells that adopt pancreatic fates. Compared to the previously disclosed protocols, such as those in U.S. Pat. Nos. 8,247,229 and 8,685,730, the present invention has significant advantages. First, it requires only 16-18 days of culture and does not require a period for the formation of embryoid bodies (EB). Second, since the cells are cultured on a polycarbonate or polyester membrane through all stages, there are no cell manipulations such as lifting cells off the culture dish, dissociating cells, or re-plating cells, all of which can contribute to cell death or alter cellular states and ultimately lead to cell loss and decreased yields.

Most importantly, as shown in Examples below, this protocol yields high levels of expression of many key pancreatic lineage transcription factor genes such as PDX1, Nkx6.1, and Ngn3, which are key endocrine progenitor genes required for correct endocrine cell specification in the pancreas. For example, PDX1 and Nkx6.1 gene expression is equivalent to that of human fetal pancreas (HFP) tissue, whereas Ngn3 and insulin gene expression is comparable, approaching that of HFP.

Moreover, the protocol produces a high percentage of insulin$^+$ cells. For example, as shown in Examples below, the cells at the end of the 4 stage culture period revealed approximately 25% insulin$^+$ cells and 8-11% are PDX1$^+$Ins$^+$ while 55-75% of cells are PDX1$^+$insulin$^-$. Also, the amount of C-peptide released into the media from differentiated cells increases significantly and progressively during the later stage of the culturing, reaching a concentration of about 1500 pM, similar to that of normal, non-diabetic humans.

A stage-by-stage description of the protocol, as well as the differentiation factors and the chemically defined media used in the protocol, is provided in the following sections. A discussion of the gene expression of the cells during each stage, especially after the final stage, is also provided as Examples to show the significant advantages of this protocol over the previous technologies. For the sake of convenience, abbreviations of the terms and phrases, as defined in Table 1, are used throughout the specification.

TABLE 1

| Abbreviation | Common Name |
|---|---|
| APS | Anterior primitive streak |
| FGF2 | Basic fibroblast growth factor |
| BMP | Bone morphogenetic protein |
| CDM | Chemically defined medium |
| CM | Conditioned medium (Mouse embryonic fibroblast - conditioned media) |
| CMBF | Conditioned medium with BMP4 and bFGF |
| EB | Embryoid body |
| ES | Embryonic stem |
| ESC | Embryonic stem cell |
| Ex-4 | Exendin 4 |
| FAB | Medium containing fibroblast growth factor, Activin A, and bone morphogenetic protein |
| FOXA2 | Forkhead box protein A2 |
| hESC | Human embryonic stem cell |
| HNF1β | Hepatocyte nuclear factor 1beta |
| HNF6 | Hepatocyte nuclear factor 6 |
| hPSC | Human pluripotent stem cells |
| hTERT | Human telomerase reverse transcriptase |
| INGAP | Islet neogenesis associated peptide |
| iPS | Induced pluripotent stem cell |
| ITS-FGF | Medium containing insulin, transferrin, selenium and fibroblast growth factor |
| ITSFAB | Medium containing insulin, transferrin, selenium, fibroblast growth factor, Activin A, and bone morphogenetic protein |
| ITSFI | Medium containing insulin, transferrin, selenium, fibroblast growth factor 7, islet neogenesis associated peptide |
| ITSFINE | Medium containing insulin, transferrin, selenium, fibroblast growth factor 7, islet neogenesis associated peptide, Nicotinamide, and exendin 4 (a long-acting GLP-1 agonist) |
| MG | Matrigel ™ |
| Mixl1 | Mix1 homeobox-like 1 |
| MEF | Mouse embryonic fibroblast |
| Nanog | Nanog homeobox |
| NB | Nicotinamide and B27 |
| NGN3 | Neurogenin-3 |
| Nkx2.5 | NK2 transcription factor related, locus 5 |
| NKX6.1 | NK6 homeobox 1 |
| NNR | Noggin-Nicotinamide-Retinoic acid |
| Oct-4 | Octamer-binding transcription factor 4 |
| PDX1 | Pancreatic duodenal homeobox 1 |
| RPMI | Roswell Park Memorial Institute Medium |
| Sox9 | SRY-box containing gene 9 |
| SSEA-3 | Stage-specific embryonic antigen 3 |
| SSEA-4 | Stage-specific embryonic antigen 4 |
| T | Brachyury (T-box transcription factor) |
| Tbx6 | T-box 6 |
| TGF-β | Transforming growth factor beta |
| TITF1 | Thyroid transcription factor 1 |
| Tra 1-60 | Tumor-related antigen 1-60 |
| Tra 1-81 | Tumor-related antigen 1-81 |
| TW | Transwell ™ |
| TWFAB | Current protocol, in which differentiation begins by seeding cells on Transwell ™ inserts at the beginning of Stage 1 |
| VEGF | Vascular endothelial growth factor |

Stage 1

In Stage 1, human pluripotent stem cells are expected to differentiate towards mesendoderm/primitive streak and definitive endoderm fates. Compared to the undifferentiated state, the mesendoderm cells at the end of Stage 1 show a significant up-regulation of at least one of the genes associated with primitive streak (Mix1 and Gsc), mesendoderm (T), and definitive endoderm (Sox17 and FOXA2).

The protocol at Stage 1 is aimed to create conditions for inducing such a differentiation. Specifically, this stage involves culturing the pluripotent stem cells, which can be either hESCs or human iPS cells in the presence of a chemically defined medium. The chemically defined medium offers conditions for inducing differentiation in the direction towards mesendoderm. In this context, the chemically defined medium comprises various growth factors and other chemical signals or compounds that may initiate differentiation of hESCs or iPSCs into progeny cell cultures of one or more particular lineage. For example, in some embodiments, the factors contained in the chemically defined medium of Stage 1 include fibroblast growth factor (FGF), Activin A, and bone morphogenetic protein (BMP).

By "fibroblast growth factors" or "FGFs" thereafter, we mean members of a family of growth factors involved in angiogenesis, wound healing, and embryonic development. FGFs are heparin-binding proteins and interactions with cell-surface-associated heparan sulfate proteoglycans have been shown to be essential for FGF signal transduction. FGFs are key players in the processes of proliferation and differentiation of wide variety of cells and tissues. For example, FGFs play an important role in mesoderm formation and are useful in the culture of stem cells with or without conditioned medium. There are several different FGF subfamilies, the member ligands of which include FGF1-FGF23. Of the known FGF ligands, all show some degree of overlap of receptor binding, with the exception of FGF11-FGF14.

In some embodiments, the FGF used in Stage 1 is selected from the group consisting of FGF2, FGF4, FGF7, FGF10 and the mixtures thereof. While FGF2 has been primarily used in this stage, our studies also have shown that other factors, including FGF4, FGF7 or FGF10, have effects comparable to FGF2 (Exhibit C). Thus, one would use any one of FGF4, FGF7 and FGF10 to replace FGF2 in Stage 1. One may also use mixtures of two or more of FGF2, FGF4, FGF7 and FGF10 in this stage. In a specific embodiment, the FGF in Stage 1 is FGF2.

For purpose of this invention, the chemically defined medium of Stage 1 comprises an effective amount of FGF. In some embodiments, the effective amount of FGF in the medium of Stage 1 ranges from about 10 ng/ml to about 200 ng/ml. For example, the effective amount of FGF may range from about 10 ng/ml to about 200 ng/ml, or from about 20 ng/ml to about 180 ng/ml, or about 30 ng/ml to about 170 ng/ml, or about 40 ng/ml to about 160 ng/ml, or about 50 ng/ml to about 150 ng/ml, or about 60 ng/ml to about 140 ng/ml, or about 70 ng/ml to about 130 ng/ml, or about 80 ng/ml to about 120 ng/ml. Preferably, the effective amount of FGF ranges from about 90 ng/ml to about 110 ng/ml. More preferably, the effective amount of FGF is about 100 ng/ml.

As used herein, as well as throughout the specification, "about" will be understood by persons of ordinary skill in the art and will vary to some extent depending upon the context in which it is used. For example, all numerical ranges herein may be understood to include all integer, whole or fractions, within the range of plus or minus 20% of the particular term.

By "Activins", we mean members of the TGF-beta superfamily, which are disulfide-linked dimeric proteins originally purified from gonadal fluids as proteins that stimulated pituitary follicle stimulating hormone (FSH) release. Activin proteins have a wide range of biological activities, including mesoderm induction, neural cell differentiation, bone remodeling, hematopoiesis and roles in reproductive physiology. Activin isoforms and other members of the TGF-beta superfamily exert their biological effects by binding to heteromeric complexes of a type I and a type II serine-threonine kinase receptor, both of which are essential for signal transduction. Activins are homodimers or heterodimers of the various beta subunit isoforms, while inhibins are heterodimers of a unique alpha subunit and one of the various beta subunits. Five beta subunits (mammalian beta A, beta B, beta C, beta E and Xenopus beta D) have been cloned to date. The activin/inhibin nomenclature reflects the subunit composition of the proteins: Activin A (beta A-beta A), Activin B (beta B-beta B), Activin AB (beta A-beta B), Inhibin A (alpha-beta A) and Inhibin B (alpha-beta B).

In some embodiments, Activins used in Stage 1 are Activin A.

For purpose of this invention, the chemically defined medium of Stage 1 comprises an effective amount of Activin A. In some embodiments, the effective amount of Activin A in the medium of Stage 1 ranges from about 10 ng/ml to about 200 ng/ml. For example, the effective amount of Activin A may range from about 10 ng/ml to about 200 ng/ml, or from about 20 ng/ml to about 180 ng/ml, or about 30 ng/ml to about 170 ng/ml, or about 40 ng/ml to about 160 ng/ml, or about 50 ng/ml to about 150 ng/ml, or about 60 ng/ml to about 140 ng/ml, or about 70 ng/ml to about 130 ng/ml, or about 80 ng/ml to about 120 ng/ml. Preferably, the effective amount of Activin A ranges from about 90 ng/ml to about 110 ng/ml. More preferably, the effective amount of Activin A is about 100 ng/ml.

By "bone morphogenetic proteins" or "BMPs" thereafter, we mean members of the transforming growth factor-β (TGFβ) superfamily of secreted signaling molecules, which play extensive pleomorphic roles in almost all aspects of embryonic development. There are several different BMP subfamilies, including, for example, BMP1, BMP2, BMP3, BMP4, BMP5, BMP6, BMP7, BMP8a, BMP8b, BMP10 and BMP15. Particularly, the relative expression level of BMP4 and other BMP family members, such as BMP2, BMP5, and BMP7 within the cell is an important determinant of BMP-induced responses. For example, BMP4 is known to play an important role in fate determination and lineage development during embryogenesis. BMP4 also inhibits early neurogenesis in murine ESC cultures and promotes pancreatic endoderm specification from uncommitted endoderm.

In some embodiments, the BMP used in Stage 1 is selected from the group consisting of BMP2, BMP4, BMP7 and the mixtures thereof. While BMP4 is used primarily in this stage, other BMPs, including BMP2, BMP7 are also believed to be comparable to BMP4. Thus, one would use any one of BMP2 and BMP7 to replace BMP4. One may also use mixtures of two or more of BMP2, BMP4 and BMP7 in this stage. In a specific embodiment, the BMP in Stage 1 is BMP4.

For the purpose of this invention, the chemically defined medium of Stage 1 comprises an effective amount of BMP. In some embodiments, the effective amount of BMP in the medium of Stage 1 ranges from about 5 ng/ml to about 50 ng/ml. For example, the effective amount of BMP may range from about 5 ng/ml to about 50 ng/ml, or from about 10 ng/ml to about 50 ng/ml, or about 20 ng/ml to about 50 ng/ml. Preferably, the effective amount of BMP ranges from about 30 ng/ml to about 50 ng/ml. More preferably, the effective amount of BMP is about 50 ng/ml.

One would appreciate that in Stage 1, as well as in other stages of this protocol, chemically defined medium may also include a basal medium containing salts, vitamins, glucose and amino acids. The basal medium can be any of a number of commercially available media. For example, a combination of Dulbecco's Modified Eagle Medium™ and Hams F12 medium, sold as a combination (DMEM/F12; Invitrogen™) may be utilized. To that combination may be added glutamine, β-mercaptoethanol, and non-essential amino acids. Other possible additives include antioxidants and lipids. A protein constituent of the medium is a serum substitute product. Albumin or purified albumin products, like the commercial product AlbuMax™ (Invitrogen™) may be used. Alternatively or in addition, a defined protein product made up of albumin, insulin and transferrin may be used. Human proteins are preferred but not essential so long as uncharacterized animal products are excluded. For example, the medium includes FGF, Activin A, and BMP in DMEM/F12 supplemented with 2% BSA, 1 mM L-glutamine, 1% nonessential amino acids, and 0.1 mM 2-mercaptoethanol.

Preferably, the duration of Stage 1 is about 3 days. However, one may adjust or modify conditions of the culturing, either chemically, physically or biologically, to accelerate or slow down the progress of cell differentiation in Stage 1, as long as the desired result of forming mesendoderm/primitive streak and definitive endoderm cells is produced at the end of this stage.

Stages 2 and 3

Once the primitive streak, mesendodermal, and definitive endodermal cells are formed, these cells are further cultured to produce posterior foregut cells at Stage 2. The cells can be characterized by increased expression of the genes including FOXA2, Sox9 and PDX1. Thus, there is a transition from endoderm-committed cells to pancreatic progenitors from Stage 1 to the end of Stage 3. The protocol at Stages 2 and 3 is designed to create conditions for inducing such progress of differentiation.

Specifically, Stage 2 involves culturing the cells in the presence of a chemically defined medium. In this stage, the chemically defined medium is obtained by adding an effective amount of FGF into insulin-transferrin-selenium (ITS) medium.

In some embodiments, the ITS medium of Stage 2, as well as those used in other stages as described below, includes about 5 μg/ml insulin, about 5 μg/ml transferrin, about 5 ng/ml selenous acid or selenium.

In some embodiments, the FGF used in Stage 2 is selected from the group consisting of FGF2, FGF4, FGF7, FGF10 and the mixtures thereof. Preferably, the FGF in this stage is selected from the group consisting of FGF2, FGF7 and the mixtures thereof.

In a specific embodiment, the FGF in Stage 2 is FGF2. In this context, the effective amount of FGF2 ranges from about 10 ng/ml to about 200 ng/ml. For example, the effective amount of FGF2 may range from about 10 ng/ml to about 200 ng/ml, or from about 20 ng/ml to about 150 ng/ml, or about 30 ng/ml to about 100 ng/ml. Preferably, the effective amount of FGF2 ranges from about 40 ng/ml to about 60 ng/ml. More preferably, the effective amount of FGF2 is about 50 ng/ml.

In another specific embodiment, the FGF in Stage 2 is FGF7. In this context, the effective amount of FGF7 ranges from about 10 ng/ml to about 200 ng/ml. For example, the effective amount of FGF7 may range from about 10 ng/ml to about 200 ng/ml, or from about 20 ng/ml to about 150 ng/ml, or about 30 ng/ml to about 100 ng/ml. Preferably, the effective amount of FGF7 ranges from about 40 ng/ml to about 60 ng/ml. More preferably, the effective amount of FGF7 is about 50 ng/ml.

Preferably, the duration of Stage 2 is about 3 days. However, one may adjust or modify conditions of the culturing either chemically, physically or biologically, to accelerate or slow down the progress of cell differentiation in this stage.

Stage 3 involves culturing the cells in the presence of a chemically defined medium. In this stage, the chemically defined medium is obtained by adding an effective amount of Noggin-Nicotinamide-Retinoic acid (NNR) into insulin-transferrin-selenium (ITS) medium.

By "Noggin" or "NOG", we mean a protein which in humans is encoded by the NOG gene. Generally, Noggin inhibits TGF-β signal transduction by binding to TGF-β family ligands and preventing them from binding to their corresponding receptors. Noggin plays a key role in neural induction by inhibiting BMP4, along with other TGF-β signaling inhibitors such as chordin and follistatin.

In some embodiments, the effective amount of Noggin used in Stage 3 ranges from about 10 ng/ml to about 1000 ng/ml. For example, the effective amount of Noggin in Stage 3 ranges from about 10 ng/ml to about 1000 ng/ml, or from about 50 ng/ml to about 900 ng/ml, or from about 75 ng/ml to about 800 ng/ml, or from about 100 ng/ml to about 700 ng/ml, or from about 125 ng/ml to about 600 ng/ml, or from about 150 ng/ml to about 500 ng/ml, or from about 175 ng/ml to about 400 ng/ml. Preferably, the effective amount of Noggin ranges from about 200 ng/ml to about 400 ng/ml. More preferably, the effective amount of Noggin is about 300 ng/ml.

By "nicotinamide" or "niacinamide" or "nicotinic acid amide", we mean the amide of nicotinic acid (vitamin B3/niacin) or its derivatives. Nicotinamide is a water-soluble vitamin and is part of the vitamin B group. Nicotinic acid, also known as niacin, is converted to nicotinamide in vivo. In cells, niacin is incorporated into nicotinamide adenine dinucleotide (NAD) and nicotinamide adenine dinucleotide phosphate (NADP), although the pathways for nicotinamide and nicotinic acid are very similar. NAD+ and NADP+ are coenzymes in a wide variety of enzymatic oxidation-reduction reactions. It is produced by the aqueous aminolysis of 3-cyanopyridine (nicotinonitrile) and subsequent crystallization.

For the purpose of this invention, the effective amount of nicotinamide used in Stage 3 is about 10 mM.

By "retinoic acid", we mean a metabolite of vitamin A (retinol) or its derivatives that mediates the functions of vitamin A required for growth and development. During early embryonic development, retinoic acid generated in a specific region of the embryo helps determine position along the embryonic anterior/posterior axis by serving as an intercellular signaling molecule that guides development of the posterior portion of the embryo. It acts through Hox genes, which ultimately control anterior/posterior patterning in early developmental stages.

In some embodiments, the effective amount of retinoic acid used in Stage 3 ranges from about 100 nM to about 10 μM. For example, the effective amount of retinoic acid ranges from about 100 nM to about 10 μM, or from about 200 nM to about 9 or from about 400 nM to about 8 μM, or from about 600 nM to about 7 μM, or from about 700 nM to about 6 μM, or from about 800 nM to about 5 μM. Preferably, the effective amount of retinoic acid ranges from about 900 nM to about 4 μM. More preferably, the effective amount of retinoic acid is about 2 μM.

Preferably, the duration of Stage 3 is about 4 days. However, one may adjust or modify conditions of the culturing, either chemically, physically or biologically, to accelerate or slow down the progress of cell differentiation in this stage, as long as at the end of Stage 3 the posterior foregut endoderm cells are produced.

Stage 4

Once the posterior foregut endoderm cells are produced, these cells can be further differentiated into pancreatic endoderm under conditions provided in Stage 4. At the end of this stage, the insulin content increased dramatically, both at transcript level and at protein level compared to Stage 3. The pancreatic endoderm cells at the end of Stage 4 can also be characterized by the expression of the genes including FOXA2, PDX1, Sox9, NKX6.1, NGN3, and Sox17.

Specifically, the protocol at Stage 4 involves culturing the posterior foregut endoderm cells in the presence of a serum free chemically defined medium. This chemically defined medium can be obtained by adding FGFs, islet neogenesis associated peptide (INGAP), nicotinamide, and Exendin-4 into ITS medium, so that the so-called ITSFINE medium is produced.

In some embodiments, the FGF in Stage 4 is FGF7. The effective amount of FGF7 ranges from about 10 ng/ml to about 200 ng/ml. For example, the effective amount of FGF7 may range from about 10 ng/ml to about 200 ng/ml, or from about 10 ng/ml to about 150 ng/ml, or from about 10 ng/ml to about 100 ng/ml, or from about 10 ng/ml to about 50 ng/ml. Preferably, the effective amount of FGF7 ranges from about 10 ng/ml to about 25 ng/ml. More preferably, the effective amount of FGF7 is about 10 ng/ml.

In some embodiments, the effective amount of INGAP in Stage 4 ranges from about 50 nM to about 500 nM. For example, the effective amount of INGAP may range from about 50 nM to about 500 nM, or from about 100 nM to about 400 nM, or from about 150 nM to about 300 nM. Preferably, the effective amount of INGAP is about 200 nM.

In some embodiments, the effective amount of nicotinamide used in Stage 4 is about 10 mM.

In some embodiments, the effective amount of Exendin-4 in Stage 4 ranges from about 1 nM to about 100 nM. For example, the effective amount of Exendin-4 may range from about 1 nM to about 100 nM, or from about 2 nM to about 80 nM, or from about 4 nM to about 60 nM, or from about 6 nM to about 40 nM, or from about 7 nM to about 20 nM. Preferably, the effective amount of Exendin-4 ranges from about 8 nM to about 15 nM. More preferably, the effective amount of Exendin-4 is about 10 nM.

In some embodiments, the chemically defined medium of Stage 4 may also contain Noggin. The effective amount of Noggin in Stage 4 ranges from about 10 ng/ml to about 300 ng/ml. For example, the effective amount of Noggin may range from about 10 ng/ml to about 300 ng/ml, or from about 20 ng/ml to about 200 ng/ml, or from about 40 ng/ml to about 100 ng/ml. Preferably, the effective amount of Noggin is about 50 ng/ml.

Preferably, the duration of Stage 4 is about 7 days. However, one may adjust or modify conditions of the culturing either chemically, physically or biologically, to accelerate or slow down the progress of cell differentiation in this stage, as long as at the end of Stage 4 the pancreatic endoderm cells are produced.

Combination of Stages

While the ultimate goal of this protocol is to induce the differentiation of pluripotent stem cells into pancreatic endoderm or pancreatic lineage, each stage of this protocol can be employed separately to achieve other desired destinations of the differentiation. For example, one may use only Stage 1 to produce mesendoderm or primitive streak and definitive endoderm cells. One may use Stage 2 or 3 to produce posterior foregut endoderm from mesendoderm. One may use Stage 4 to produce pancreatic endoderm from posterior foregut cells.

Also, one may choose to combine one stage with one or more other stages of this protocol. For example, one may combine Stage 1 to Stage 3 to produce posterior foregut endoderm. This combination has several commercial embodiments. For example, the combination of Stage 1 to 3 could be used as the platform for drug screening for compounds/small molecules, which stimulate the growth of new beta cells from pancreatic progenitors or compounds or which promote progenitor cell survival, proliferation, or beta cell regeneration. The combination may also be a cell/tissue transplant platform, that is, transplant progenitor cells, and non-functional beta cells, alone or in combination, in a device or in combination with other cells or matrix. Additionally, the combination of these stages that generates pancreatic progenitor cells could be the in vitro or in vivo platform for differentiation of beta cells using a culture medium that is entirely different from ours.

One may combine Stages 3 and 4 to produce pancreatic endoderm from posterior foregut cells. For example, one could use an entirely different culture conditions for developing endoderm and pancreatic progenitors, and then could use Stages 3 and 4 media to promote maturation of their endoderm and pancreatic progenitors, which could then be used as a platform for drug discovery or therapeutic transplantation. Alternatively, these media could be used to promote maturation of fetal pancreas tissue, or improved culture conditions for human islets in vitro.

One may also combine all four stages. Such a combination could be the platform for generation of terminally differentiated beta-like cells, that is, one may use Stages 1-4 and then add on their own stages or additional steps for either therapeutic transplantation or drug discovery. Whereas the progenitors are a platform for identifying compounds that stimulate growth and differentiation to beta cells from pancreatic progenitors, the terminally differentiated cells would be used in a different assay. These would be used for identifying drugs coming to clinical trials to test for potential toxicity to beta cells or inhibition of beta cell functions, such as insulin synthesis and secretion.

Extracellular Matrix and Polycarbonate or Polyester Membrane

Preferably, a typical extracellular matrix is used in all stages of the protocol. Extracellular matrix is a gelatinous protein mixture that may help cells form three dimensional structures to promote cell-cell contact and create a more islet-like environment. In one embodiment, the extracellular matrix is Matrigel™, which is secreted by Engelbreth-Holm-Swarm (EHS) mouse sarcoma cells. The extracellular matrix can be further contemplated to comprise various other extracellular matrix components, including combinations of extracellular matrix components, gelling agents, proteins, and optionally growth factors.

The extracellular matrix can be obtained by any methods known in the art. In some embodiments, the matrix is one of laminins Laminins are trimeric proteins that contain an α-chain, a β-chain, and a γ-chain, found in five, four, and three genetic variants, respectively. The laminin molecules are named according to their chain composition, for example, laminin-111, laminin 411, laminin-511 and laminin-521. In a specific embodiment, the matrix is laminin-511. In some other embodiments, the matrix is one of commercial products, such as Matrigel™.

In some embodiments, the extracellular matrix may be further coated on a polycarbonate or polyester membrane. For example, the polycarbonate or polyester membrane can be a variety of porous substrates, including, but not limited to TransWell™ inserts. The polycarbonate or polyester membrane may contain any physiologically acceptable substrate materials upon which human pluripotent stem cells may be cultured, for example, polyester and polycarbonate, but any other suitable materials may be used as well. Additionally, the porous substrates may be either a relatively soft material, such as a membrane or other pliable material, or a hard material that resists bending.

By using extracellular matrix and polycarbonate or polyester membrane, the protocol avoids multiple substrate changes during cell culturing. In a specific embodiment, human pluripotent stem cells, hESCs, are seeded on Matrigel™-coated TransWell™ inserts in the presence of a suitable chemically defined medium.

Differentiation Markers

By measuring expression of particular genes and proteins, progress of differentiation of pluripotent stem cells, such as hESCs and iPS cells, toward the pancreatic lineage may be detected and their progression monitored. For example, pancreatic duodenal homeobox 1 (PDX1) is a transcription factor specifying the pancreatic lineage. The forkhead/winged helix transcription factor FOXA2 (formerly HNF-3β) is an upstream regulator of PDX1 and is a marker of definitive endoderm. The Sry/HMG box transcription factor Sox9 is expressed in the early pancreatic epithelium (uncommitted pancreatic progenitor cells). Earlier in differentiation, Sox17 is a marker of the definitive endoderm, but is not expressed later in differentiation. Sox17 is also expressed in primitive endoderm. Neurogenin 3 (ngn3) is an indicator of endocrine cell specification in the embryonic pancreas and induction of a neuroendocrine cell differentiation. NKX6.1 is a homeobox protein required for the development of β cells in the pancreas.

The cells at each stage of the protocol can be characterized by the expression of particular genes. For example, mesendoderm cells are defined by the expression of Brachyury ("T"), expression of goosecoid (Gsc), Mix11, FOXA2, and/or Sox17. Pancreatic lineage cells include, for example, cells co-expressing PDX1 and NKX6.1, which are well known to represent either pancreatic epithelial progenitor cells or β cells. Suitable terminally differentiated cells may also be characterized by the simultaneous expression of insulin, C-peptide and PDX1. Other cell types of the endocrine lineage, such as glucagon-expressing cells (for example, α-cells) and somatostatin-expressing delta cells may appear in this context and in these regions of the cultures as well. Pancreatic lineage cells are the cell types in the body such as those expressing PDX1, insulin, and C-peptide, which are well known to be simultaneously expressed in normal cells, or cells expressing somatostatin generally understood to represent delta cells. Under the present protocol, the transition from mesendoderm to pancreatic lineage cells is posterior foregut cells, which may be characterized by expression of the genes including FOXA2 and/or Sox9.

In a related aspect, the present invention also provides cell populations comprising posterior foregut cells and/or pancreatic lineage cells is prepared by methods described above.

In another related aspect, the present invention provides methods of using the cell population prepared by using the cell culture methods described above for drug screening, comprising the step of (a) exposing the cells to a drug; and (b) observing whether the drug promotes progenitor cell survival or proliferation or beta cell regeneration.

In another related aspect, the present invention provides methods of using the cell population prepared by using the cell culture methods described above for a cell/tissue transplant, comprising the step of transplanting the progenitor cells into a mammalian patient.

The following examples are provided as further non-limiting illustrations of particular embodiments of the invention.

EXAMPLES

Example 1

Protocol

The genes and intercellular signaling molecules controlling definitive endoderm and pancreas development in vertebrates are rapidly being elucidated. This knowledge has informed the establishment of methods for generating such cells from human ES and iPS cells in vitro. Based on the defined roles of nodal/Activin signaling in definitive endoderm development, we have identified a protocol using Activin A, BMP, and FGF in chemically defined, serum-free media which efficiently directs human pluripotent stem cells into a homogeneous population of foregut and pancreatic progenitors, including PDX1 and Sox9 expressing cells. Under defined conditions, a proportion of progenitors ultimately gives rise to insulin $^+$C-peptide$^+$/PDX1$^+$/β-like cells as well as cells expressing other endocrine hormones in vitro.

Cells

Cultures of undifferentiated hESCs or human iPS (hiPS) cells were used. Cell lines used were NIH-approved H1 (WA01) and H9 (WA09) between passage 18 and 42, though hiPS cell lines, including those derived from iPS (IMR-90)-4-MCB-1, iPS(Foreskin)-1-MCB-1, and DF 19-9-7T-MCB-01 may be used, as well as mouse ES cells.

Media

Table 3 lists the components of the culture medium used in each Stage of this protocol.

TABLE 3

| Culture Media |
|---|
| Stage 1 Exemplary Culture Medium |
| DMEM/F12 (Invitrogen, 11330-057) |
| 100 ng/ml bFGF (Invitrogen PHG0021) |
| 100 ng/ml ActivinA (R&D 338-AC-050) |
| 50 ng/ml BMP4 (R&D 314-BP) |
| 1 g of BSA (final conc. 2% w/v) (Sigma, A7030) |
| 0.5 mL L-glutamine (1%, final conc. 2 mM) (Invitrogen, 25030-081) |
| 0.5 mL nonessential amino acids (1%, final conc. 1 mM) (Invitrogen, 11140) |

TABLE 3-continued

Culture Media 100 uL 2-mercaptoethanol (final conc. 0.11 mM)
(Invitrogen, 21985)
Stage 2 Exemplary Culture Medium DMEM/F12 (Invitrogen, 11330-057)
ITS (Fisher, CB-40351, containing about 5 μg/ml insulin, about
5 μg/ml transferrin, about 5 ng/ml selenous acid)
50 ng/ml FGF7 (R&D 251-KG-050)
Stage 3 Exemplary Culture Medium DMEM/F12 (Invitrogen, 11330-057)
ITS (Fisher, CB-40351, containing about 5 μg/ml insulin, about
5 μg/ml transferrin, about 5 ng/ml selenous acid)
2 uM Retinoic Acid (Sigma, R2625-50MG)
300 ng/ml Noggin (R&D 6057-NG-100)
Stage 4 Culture Medium DMEM/F12 (Invitrogen, 11330-057)
0.2 g BSA (Final conc. 0.2% w/v) (Sigma, A7030)
ITS (Fisher, CB-40351, containing about 5 μg/ml insulin, about
5 μg/ml transferrin, about 5 ng/ml selenous acid)
10 ng/ml FGF7 (R&D 251-KG-050)
200 nM INGAP(PSN-4765), UW-Madison
10 mM nicotinamide, (Sigma, N0636-100 g)
10 nM exendin-4 (Sigma, E7144-1 mg)
4 μg/ml insulin (Invitrogen, 12585-014)

Preparation of Undifferentiated Cells and Matrigel™ Coated Plates

We cultured undifferentiated human embryonic stem cells (hESCs) or human induced pluripotent stem cells (hiPSCs) under standard conditions in stem cell media. The cells were cultured in a 6 well plate in mTeSR™ media on Matrigel™ (1 mg/6 well). Cells were ready for Stage 1 when ~80-90% confluent. We have also used cells cultured in Essential 8™ medium (E8) on Matrigel™ to start the differentiation.

We prepared Matrigel™ coated plates the day before initiating differentiation culture. One aliquot of growth factor-reduced Matrigel™ (1 mg/tube) was thawed and diluted with 3 ml cold DMEM/F12. 0.15 ml of diluted Matrigel™ was added to the 12 Transwell™ inserts. The plate with inserts was placed at 4° C. overnight.

On the day of splitting, the Matrigel™ coated plate was allowed to sit at room temperature for at least one hour prior to use. Before adding cells, remaining Matrigel™ solution was aspirated from the inserts and the inserts were washed once with PBS. The aspirated PBS and 0.5 ml of mTeSR™ were added to the lower compartment. The upper compartment was filled with the cell suspension.

When undifferentiated ES cells are 80-90% confluent they were detached by adding 1 ml of 2 mg/ml dispase to each well. They were incubated at 25° C. and observed under the microscope until the edges of colonies began to fold. The dispase was aspirated carefully. and the cells washed well once with PBS. Two wells of a 6-well plate is the proper amount for a single 12 well plate. When cells are cultured in E8 instead of mTeSR™, EDTA is used to detach them from the plate.

We collected the cells into a 15 ml conical tube by gently rinsing and scraping with 2 ml of mTeSR™. We rinsed the well with an additional 2 ml of mTeSR™. The cells were then centrifuged for 3 minutes at 1000 rpm to pellet cells. The pellet was compact and not dispersed.

We carefully aspirated the supernatant. We then added 4 ml mTeSR™ to the pellet and pipetted to disperse. The size of clusters/colonies was ~200-500 um.

We added 0.3 ml of cell suspension to each of the Matrigel™ coated inserts (as prepared above).

To distribute the cells evenly, the plate was quickly shaken several times in a side-to-side and back-and-forth motion (i.e. in the x and y planes). The plate must not be swirled, as this will cause the cells to cluster in the center.

We cultured cells overnight at 37° C. on an incubator rack.

The cells were examined by microscopy 24 hours after passaging. While two wells of a 6-well plate should be sufficient to create a confluent monolayer of cells in the inserts sometimes there is poor attachment. If this occurred, we changed mTeSR™ medium daily until cells reached 80% confluence.

Cell Culturing

A brief summary of the protocol is provided in FIG. 1.

Stage 1 Day 0-2: Twenty-four hours after splitting, Stage 1 medium was prepared and brought to room temperature. Spent medium was then aspirated from both the upper and lower compartments. 0.5 ml Stage 1 medium was then added to the lower compartment and 0.3 ml Stage 1 media added to the upper compartment. The medium was exchanged daily as described above and between medium changes cells were cultured at 37° C. on an incubator rack.

Stage 2 Day 3-5: On day 3, Stage 2 medium was prepared and brought to room temperature. The spent medium was then aspirated from both the upper and lower compartments. 0.5 ml Stage 2 medium was then added to the lower compartment and 0.3 ml Stage 2 medium added to the upper compartment. The medium was exchanged daily as described above and between medium changes cells were cultured at 37° C. on an incubator rack.

Stage 3 Day 6-9: On day 6, Stage 3 medium was prepared and brought to room temperature. The spent medium was then aspirated from both the upper and lower compartments. 0.5 ml Stage 1 medium was then added to the lower compartment and 0.3 ml of Stage 2 medium added to the upper compartment. The medium was exchanged daily as described above and between medium changes the cells were cultured at 37° C. on an incubator rack.

Stage 4 Day 10-18: On day 10, Stage 4 medium was prepared and brought to room temperature. The spent medium was then aspirated from both the upper and lower compartments. 0.5 ml of Stage 4 medium was added to the lower compartment and 0.3 ml of Stage 4 medium added to the upper compartment. The medium was exchanged daily as described above and between medium changes cells were cultured at 37° C. on an incubator rack.

Example 2

Results

An analysis of the gene expression of the cells cultured under conditions of the present protocol, as well as a comparison to those of the cells cultured under conditions of the previously disclosed protocols in U.S. Pat. No. 8,247,229 and U.S. Patent Application Publication No. 2012/0264209 and other protocols known in the art, is described below. A number of terminologies or acronyms have been used to describe these protocols, as summarized in Table 3 below.

TABLE 3

Summaries of Protocols

| | Other names |
|---|---|
| Current Protocol | TW-FAB, or FAB/ITS-FGF7/ITS-NNR/ITSFINE-Noggin-continuous on TW (total culturing time: 18 days) |

TABLE 3-continued

Summaries of Protocols

| | Other names |
|---|---|
| Previous Protocol | FAB, or the standard protocol disclosed in U.S. Patent Application Publication No. 2012/0264209, or FAB/MEF-CM/ITS-bFGF/ITSFINE/RPMI-NB-no TW (total culturing time: 49 days) |
| Simplified Protocol | The simplified protocol disclosed in U.S. Patent Application Publication No. 2012/0264209, or FAB/ITS-bFGF/ITSFINE- continuous on TW (total culturing time: 32 days) |

Figure 2:
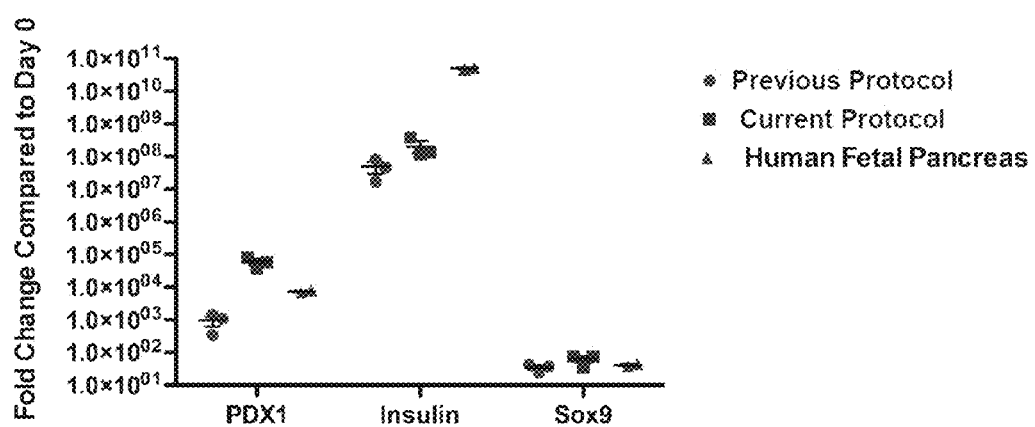
FIG. 2 shows that the cell culture using the present protocol has higher PDX1 and insulin expression than the previously disclosed protocol.

Cells Developed Under the Current Protocol have Higher PDX1 and Insulin Expression than Cells Grown Under Previous Protocols QPCR was performed at the end of Stage 4 (Day 50 or Day 18) to examine gene expression of PDX1, a marker of pancreatic epithelium and progenitor cells, insulin, a marker of beta cells, and Sox9 which is expressed in the developing pancreatic epithelium. The gene expression is compared to undifferentiated cells collected at Day 0 and β-Actin is the internal control. As shown in FIG. 2, the fold change is graphed logarithmically. Cells differentiated using the current protocol have significantly higher PDX1 and insulin gene expression than comparison protocol. Human Fetal Pancreas (HFP), gestation 14-20 weeks, is represented as a positive control.

Figure 3:
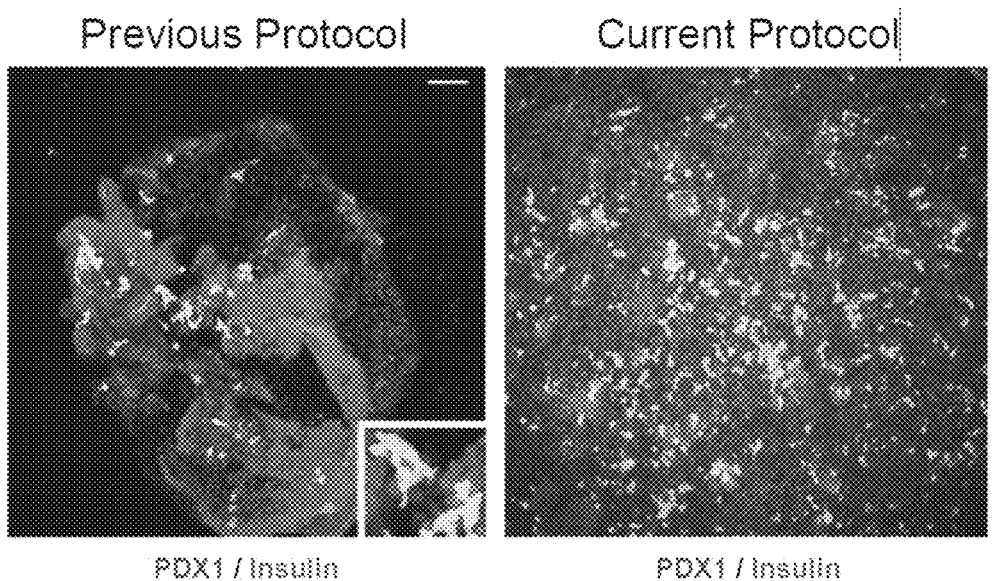
FIG. 3 are images showing the cell culture using the present protocol has higher PDX1 and insulin expression than the previously disclosed protocol.

Immunofluorescence miscroscopy was also performed at the end of Stage 4 (Day 50 in the case of the prior protocol or Day 18 in the case of the current protocol) to examine protein expression of PDX1 and insulin. As shown in FIG. 3, there is an increased amount of insulin and PDX1 protein expression compared to the first generation protocol. Additionally, since there is no cell manipulation the PDX1 and insulin protein expression is more wide spread.

Figure 4:
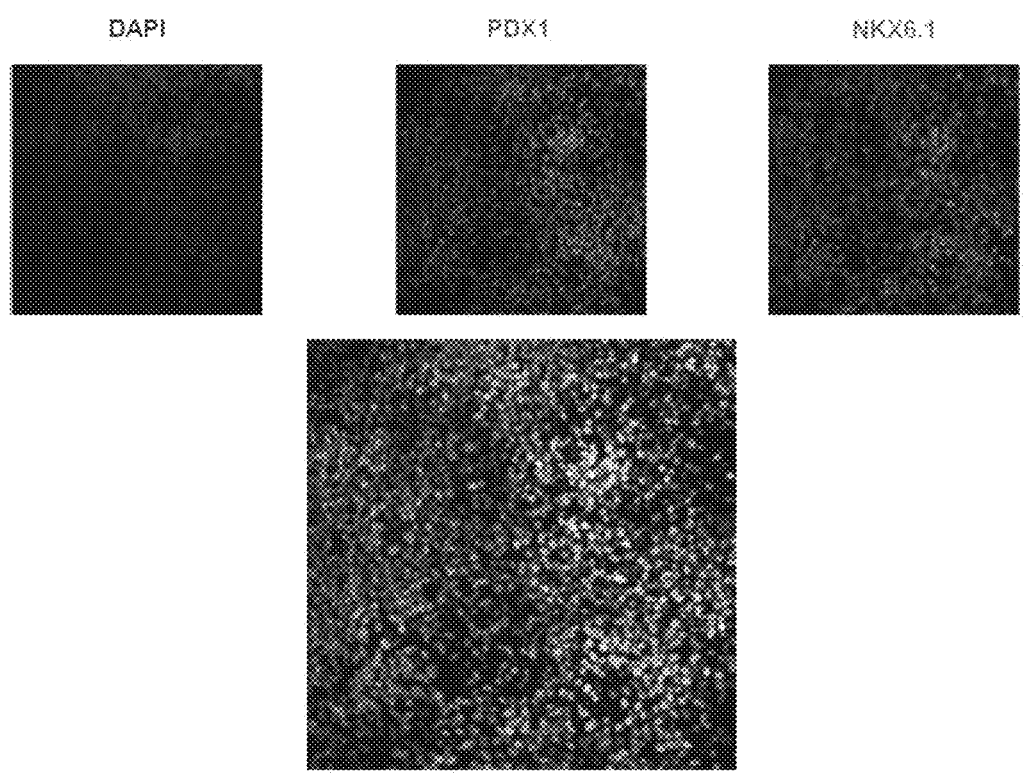
FIG. 4 are images showing the cell culture using the present protocol has increased PDX1 and NKX6.1 co-expression levels.

Cells Developed Under the Current Protocol Demonstrate Increased PDX1 and NKX6.1 Co-Expression Immunofluorescence microscopy was performed at the end of Stage 4 (Day 18) to examine protein expression of PDX1 and NKX6.1, a marker of pancreatic progenitors, and endocrine specification to beta cells. Both markers are also expressed in the mature beta cells. As shown in FIG. 4, there is significant expression of NKX6.1 that is widespread and co-localizes with PDX1 positive cells.

Figure 5:
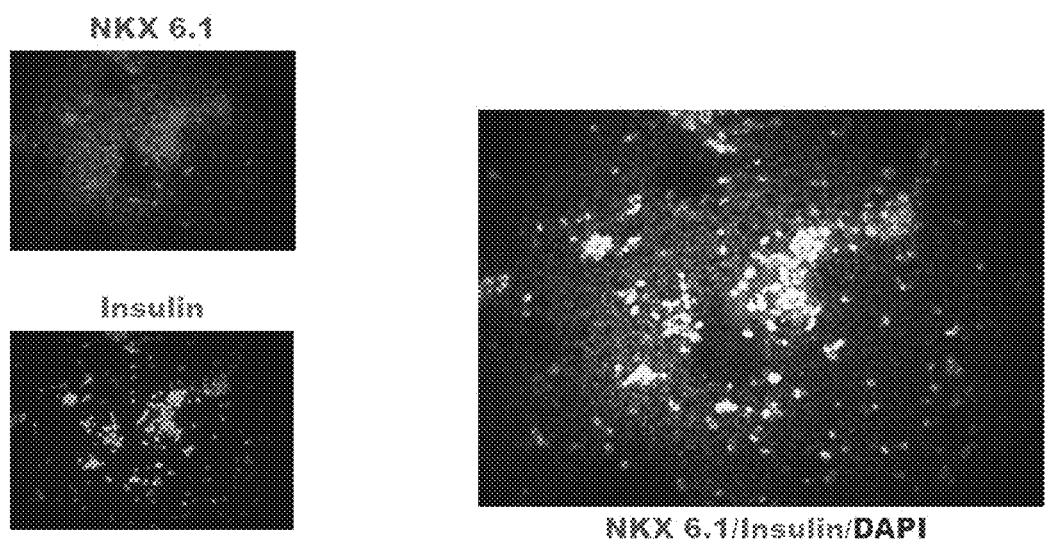
FIG. 5 are images showing the cell culture using the present protocol has increased insulin and NKX6.1 co-expression levels.

The Current Four Stage Protocol Shows Increased Insulin and NKX6.1 Co-Expression Immunohistochemistry was performed at the end of Stage 4 (Day 18) to examine protein expression of Insulin and NKX6.1. As shown in FIG. 5, there is significant expression of NKX6.1 that is widespread and co-localizes with insulin positive cells.

Comparison of the Current Four Stage Protocol to Betalogics Protocol

Figure 6:
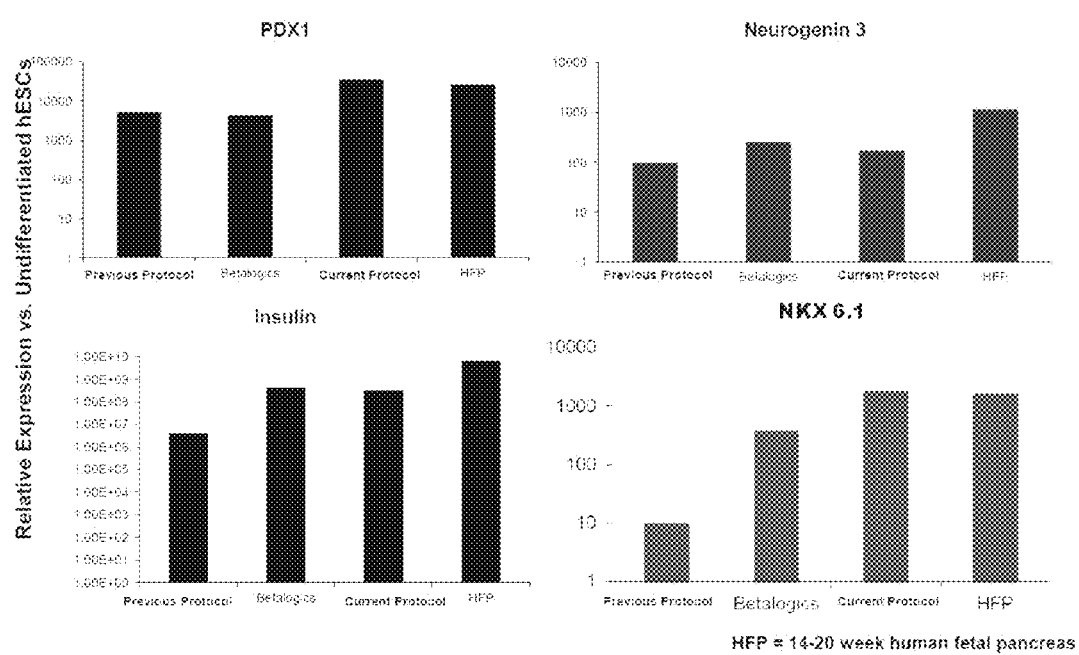
FIG. 6 is the comparison of the expression levels of PDX1, neurogenlin 3, insulin and NKX6.1 between the present protocol and the previously disclosed protocol.

QPCR was performed at the end of Stage 4 to examine gene expression of PDX1, insulin, Neurogenin 3, a marker of endocrine progenitor cells and NKX6.1. The gene expression is compared to undifferentiated cells collected at Day 0 and B-Actin is the internal control. As shown in FIG. 6, the fold change is graphed logarithmically in all four graphs. The current protocol when compared side by side with the Betalogics protocol (Rezania A. et al., Maturation of Human Embryonic Stem Cell-Derived Pancreatic Progenitors Into Functional Islets Capable of Treating Pre-existing Diabetes in Mice, Diabetes, 2012 (61): 2016-2029) has higher PDX1 and NKX 6.1 expression and comparable levels of Neurogenin 3 and insulin expression.

Figure 7:
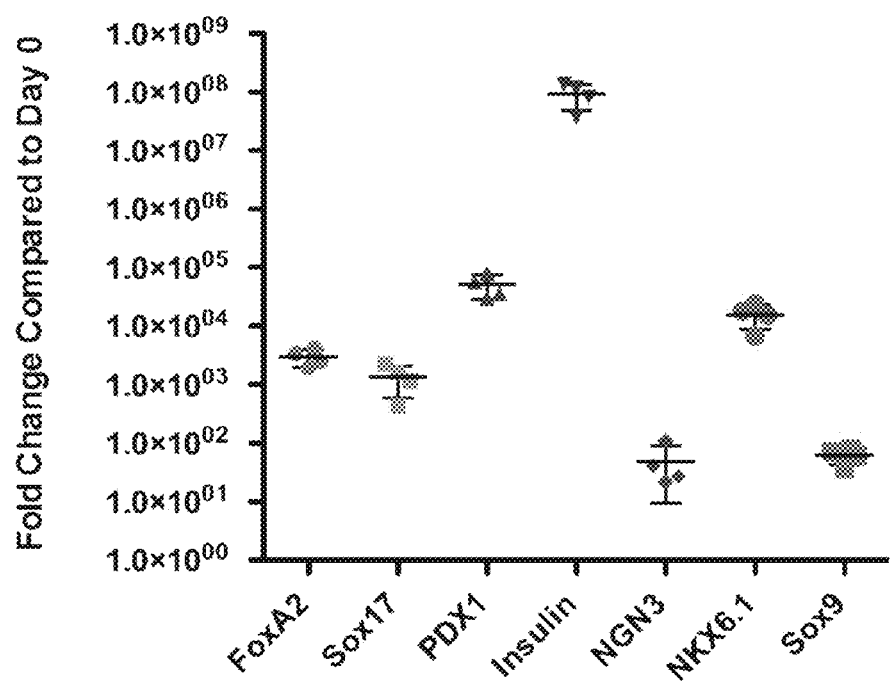
FIG. 7 shows the present protocol provides consistent and reproducible pancreatic gene expression levels.

The Current Protocol Provides Consistent and Reproducible Pancreatic Gene Expression QPCR was performed at the end of Stage 4 (Day 18) to examine gene expression of key endoderm and pancreatic markers. The gene expression is compared to undifferentiated cells collected at Day 0 and B-Actin is the internal control. As shown in FIG. 7, the fold change is graphed logarithmically. In summary, the gene expression of all the key endoderm and pancreatic markers we examined is highly reproducible.

Quantification of PDX1 and Insulin Expression by Flow Cytometric Analysis

Figure 8:
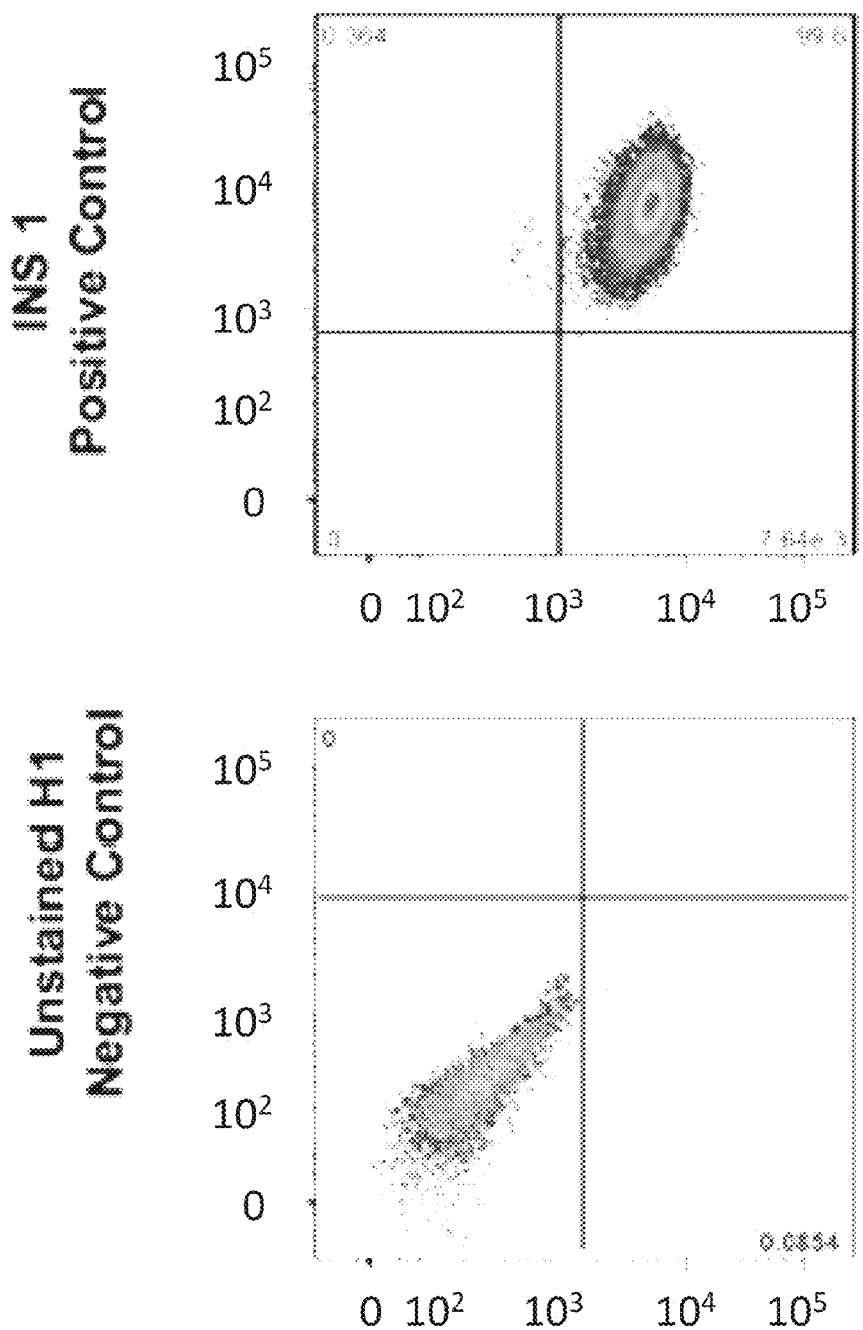
FIG. 8 is image quantification of PDX1 and insulin expression by flow cytometric analysis.

To quantify insulin and PDX1 protein expression we optimized a flow cytometry assay. As shown in FIG. 8, on the top left of this figure is the positive control. The INS-1 cell line is an immortalized pancreatic beta cell line that expresses both PDX1 and insulin. On the bottom left, is our negative control, unstained H1 cells differentiated for 18 days. On the right, is H1 cells differentiated by the current protocol through day 18 stained with Insulin-PB and PDX1-AF488. It shows that approximately 78% of the cells are PDX1 positive and 19% are insulin positive. Only 8-11% of the cells are PDX1 and insulin double positive.

Figure 9:
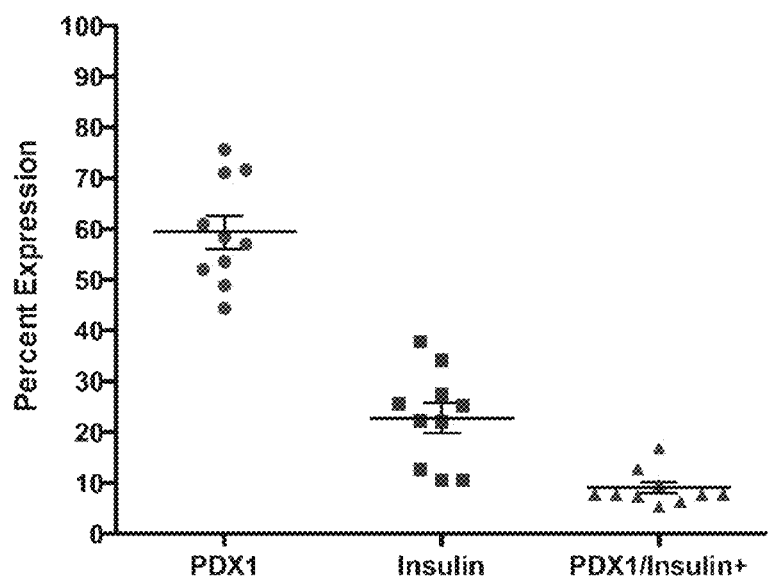
FIG. 9 is quantification of PDX1 and insulin expression by flow cytometric analysis.

Importantly, the flow cytometry results are reproducible. As shown in FIG. 9, graphed on the y axis is the percent of total cells expressing these proteins and the x axis depicts the condition being examined. Each dot represents an individual replicate representative of three separate experiments. The line is the average with the standard error of the means plotted. The average of PDX1 positive cells is 59.45%, the average insulin positive cells is 22.99%, the average PDX/Ins positive cells is 8.49%.

The Current Protocol Produces Cells that can Process Proinsulin to C-Peptide

Figure 10:
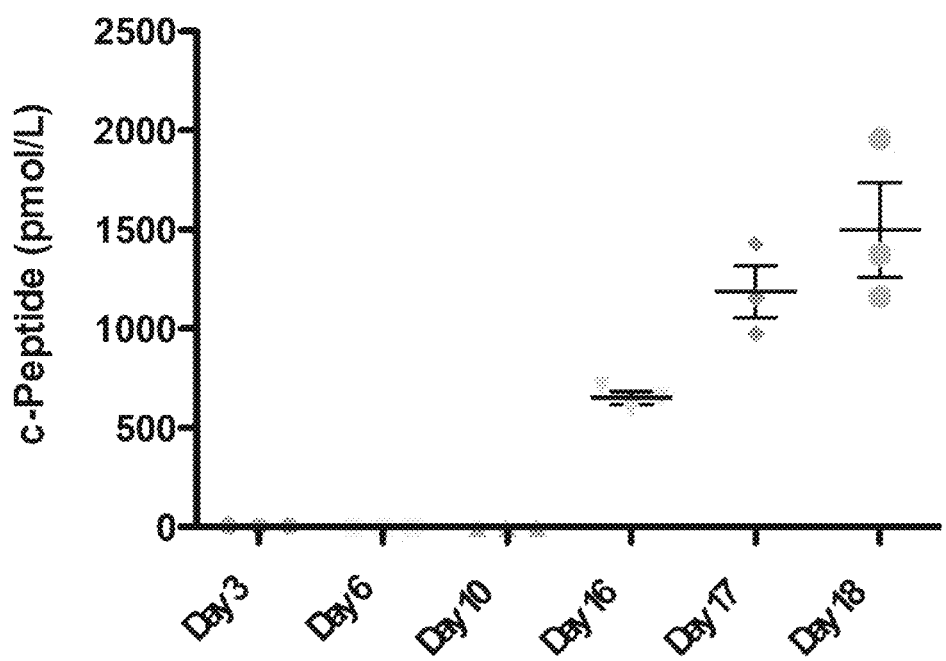
FIG. 10 shows that the cell culture using the present protocol has cells that can process proinsulin to c-peptide.

A C-peptide ELISA was performed at several culture timepoints. C-peptide, is a short 31-amino-acid protein that connects insulin's A-chain to its B-chain in the proinsulin molecule. Thus, measuring C-peptide levels is a way to measure whether or not there are functional cells that are processing insulin. As shown in FIG. 10, we found that the medium contained significant and functional levels (meaning similar to human serum levels) of C-peptide at multiple timepoints during Stage 4 but not prior, suggesting that the cells that develop later in the cultures are able to process insulin.

A Majority of Cells Co-Express Insulin and Glucagon

Figure 11:
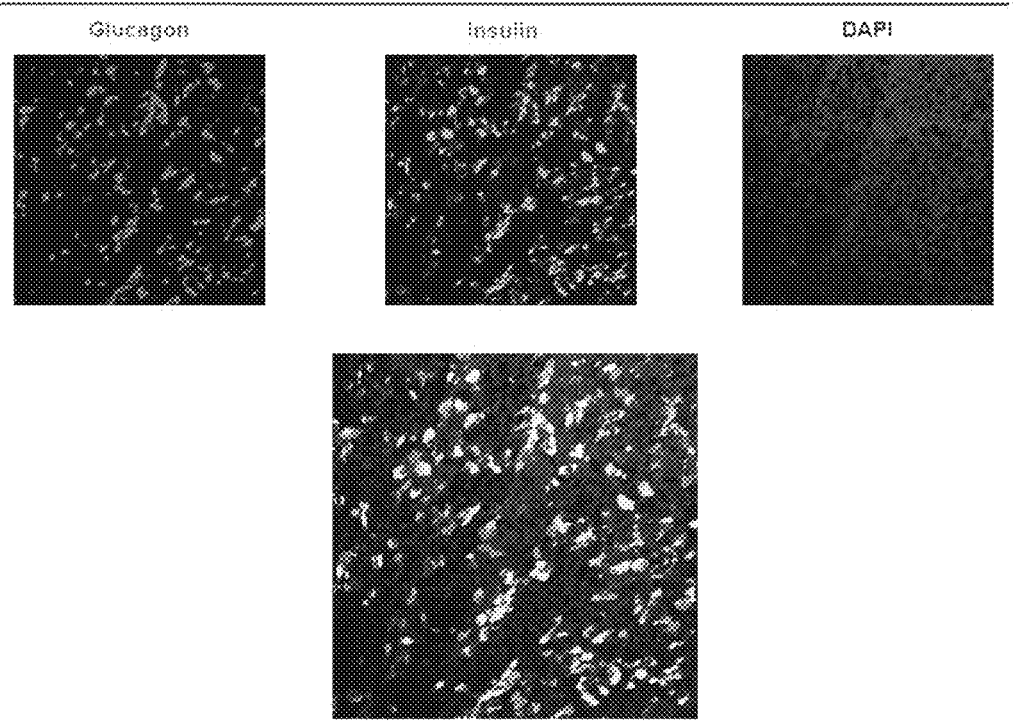
FIG. 11 are images showing that a majority of cells co express insulin and glucagon.

We also examined if the cells were monohormonal. As shown in FIG. 11, glucagon is in red and insulin is in green. Co-stained cells appear in yellow. A majority of the cells co-express insulin and glucagon suggesting that the cells that are generated are polyhormonal and therefore may not be fully mature.

The Cells are not Glucose Responsive at Either Day 14 or Day 18

Figure 12:
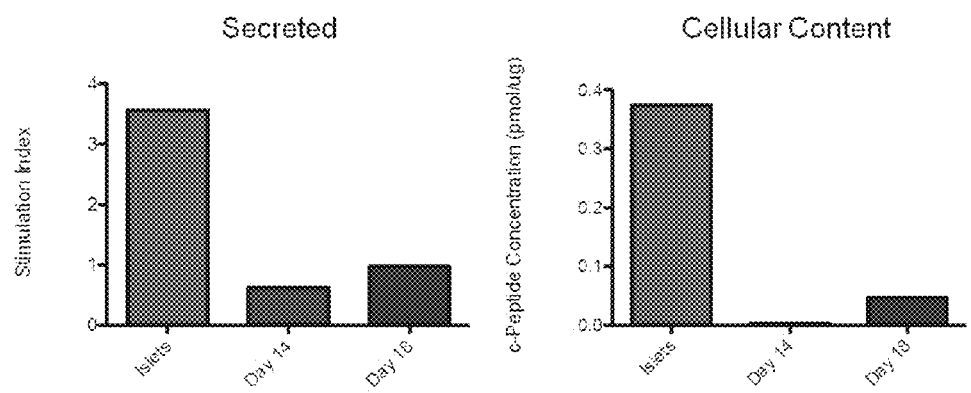
FIG. 12 shows that the cell culture using the present protocol are not glucose responsive at either day 14 or day 18.

Left panel of FIG. 12 shows the results of the experiment to assess glucose stimulated insulin secretion. A stimulation index greater than 1.8-2 is considered normal. Stimulation index is the amount of C-peptide measured in the supernatant (i.e., released/secreted) after an about 30 minutes to 1 hour incubation in high glucose divided by the amount secreted in response to incubation at low glucose for about 30 minutes to 1 hour. Islets in the gray bar are isolated human islets as a positive control. The results show that neither Day 14 nor Day 18 FAB-TransWell™ cultured cells secrete measurable amounts of C-peptide in response to a high glucose challenge.

Right panel of FIG. 12 shows the results of the experiment to assess cellular content of C-peptide. Cells were collected and protein isolated and protein mixture was added to a human C-peptide ELISA assay. Human islets were the positive control. Neither Day 14 nor 18 FAB-TransWell™ cultured cells contained a significant amount of C-peptide normalized to total ug protein to account for possible differences in the amount of cellular material assayed.

Expression of Pancreatic Markers Occurs Differentially

Figure 13:
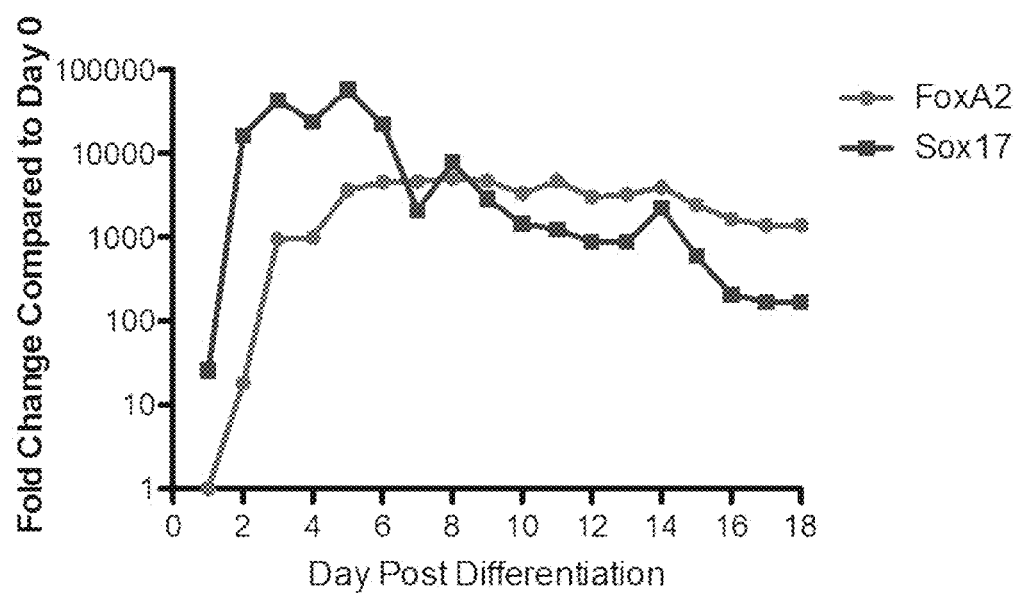
FIG. 13 shows that the expression of pancreatic markers FoxA2 and Sox17 occurs differentially.

We performed several time course studies to examine both gene and protein expression. To examine gene expression, QPCR samples were collected every day. The gene expression is compared to undifferentiated cells collected at Day 0 and B-Actin is the internal control. As shown in FIG. 13, the fold change is graphed logarithmically. FOXA2 and Sox17 are two definitive endoderm markers and both are rapidly activated (Day 2 and 3 respectively) with expression levels remaining elevated through the remainder of the protocol.

Figure 14:
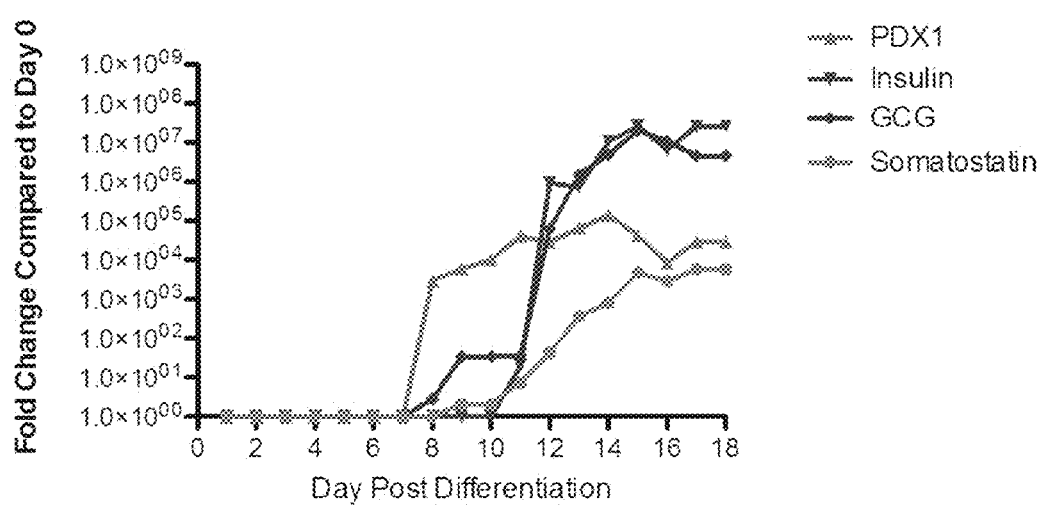
FIG. 14 shows that the expression of pancreatic markers PDX1, insulin, GCG and somatostatin occurs differentially.

Also, as shown in FIG. 14, PDX1 gene expression is increased as early as Day 8 and remains increased throughout the remainder of the protocol. The pancreatic hormones are elevated approximately 4 days later on Day 12, with somatostatin lagging behind glucagon and insulin a little.

Figure 15:
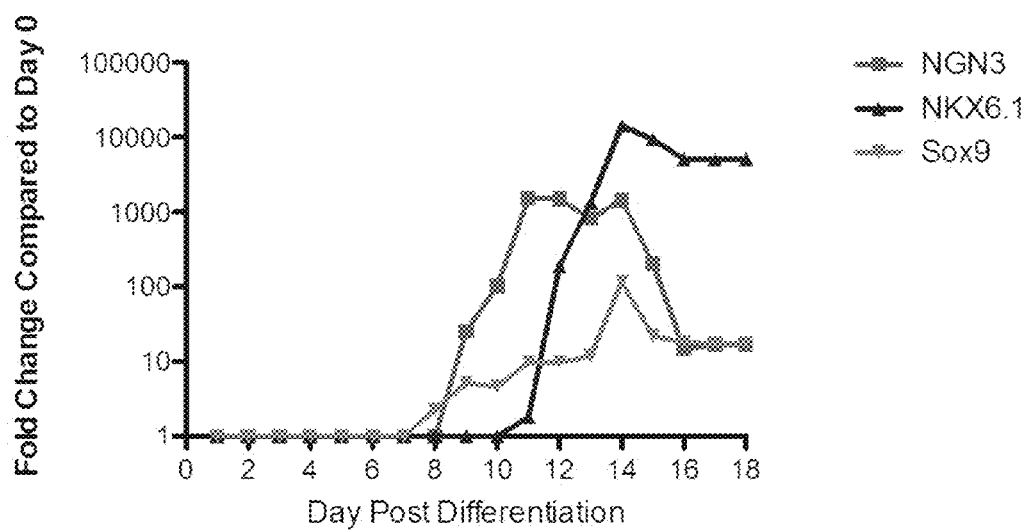
FIG. 15 shows that the expression of pancreatic markers NGN3, NKX6.1 and Sox9 occurs differentially.

Finally, as shown in FIG. 15, examination of the final three genes revealed that Neurogenin 3 expression increases at Day 10 but begins to decrease after Day 14. Interestingly, NKX6.1 expression increases in a similar manner to insulin beginning at Day 12. Sox9 expression increases similarly to PDX1 expression and remains elevated through the remainder of the protocol.

Analysis of PDX1 and Insulin Protein Expression

Figure 16:
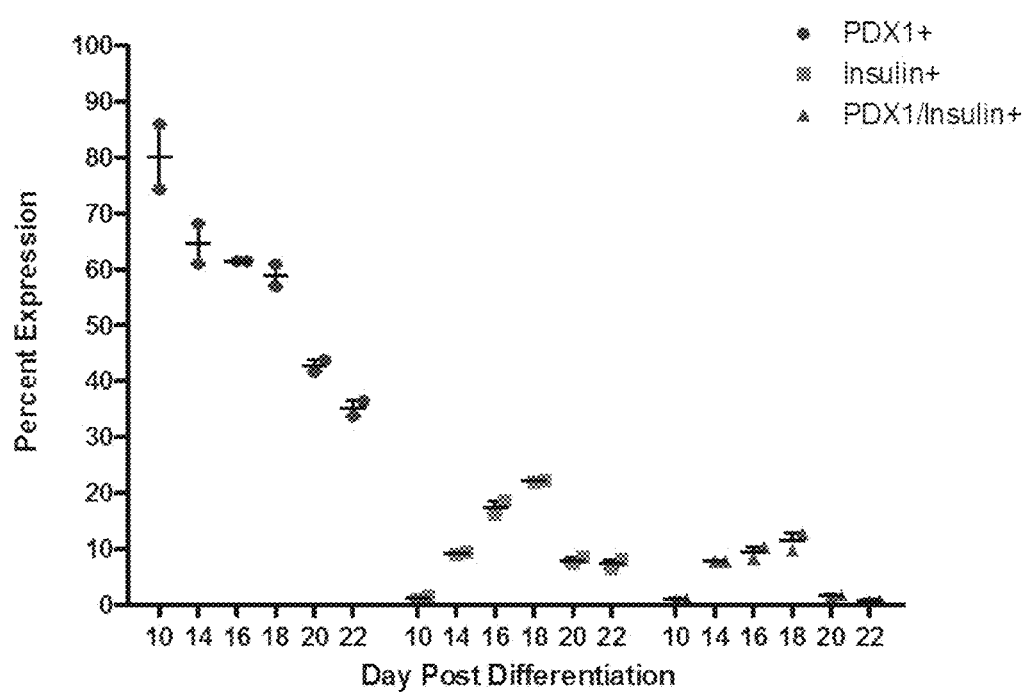
FIG. 16 is an analysis of PDX1 and insulin protein expression.

To examine PDX1 and insulin protein, expression timepoints were collected every other day and run by flow cytometry. As shown in FIG. 16, graphed on the y axis is the percent expression and the x axis depicts the condition being examined. Each dot represents an individual replicate. The line is the average with the standard error of the means plotted. Examination of protein expression revealed that PDX1 is expressed as early as Day 10 (end of Stage 3). By Day 14, PDX1 expression is about 10% lower and continues to decrease, most drastically at Day 20. In contrast insulin protein expression is not detected until Day 14 and continues to increase until Day 18. Double positive cells are first detected at Day 14 and remain at a similar level until Day 18. Following Day 20 there is a significant loss of double positive cells.

Loss of PDX1 and Insulin$^+$ Cells Increases Significantly by Day 22

Figure 17:
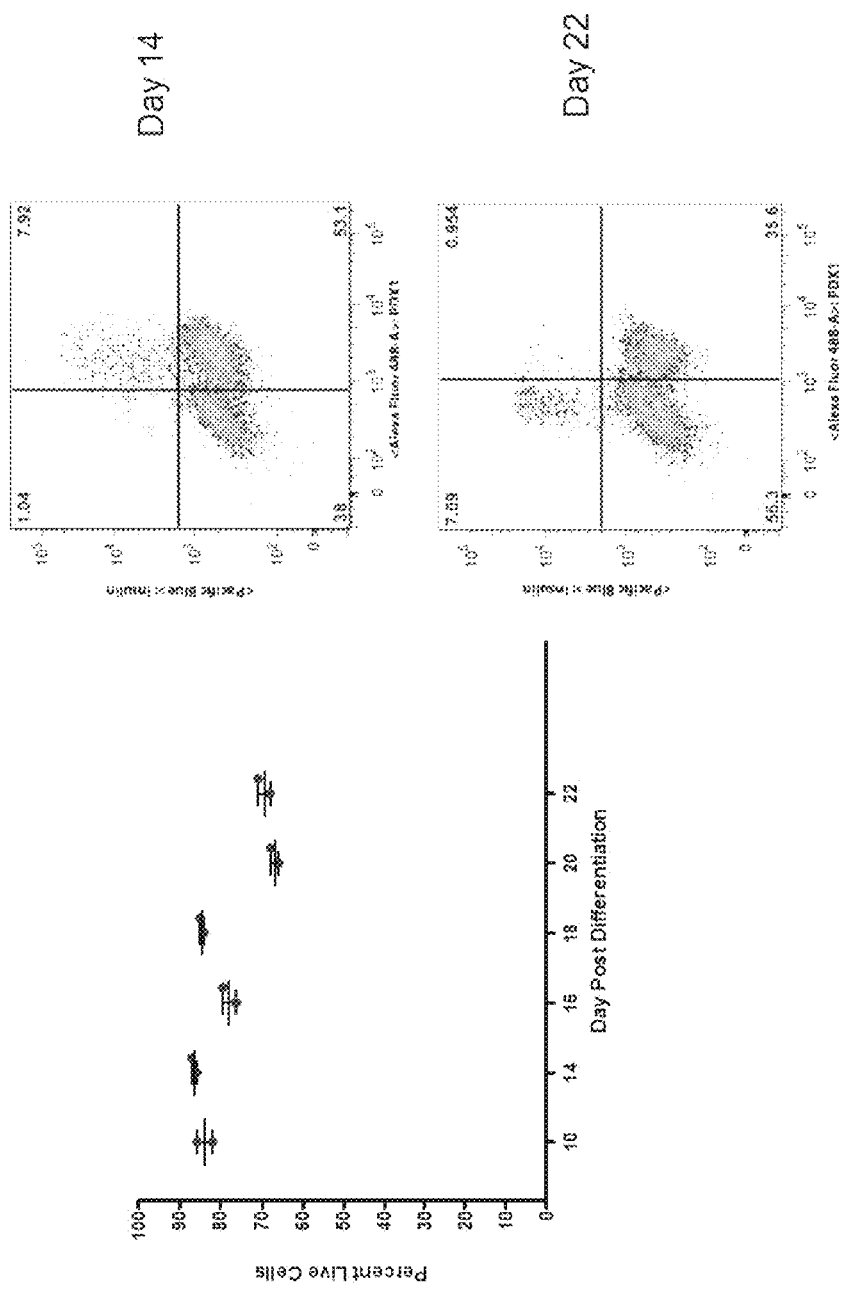
FIG. 17 shows loss of PDX1 and insulin$^+$ cells increases significantly by day 22.

In addition to examining PDX1 and insulin expression, we also examined cell death. As shown in FIG. 17, approximately 90% of the cells are viable from Day 10-18. At Day 20-22 only about 70% of the cells are viable. A majority of the cells that are dying express PDX1 and insulin.

The Current Four Stage Protocol does Work with iPS Cells

Figure 18:
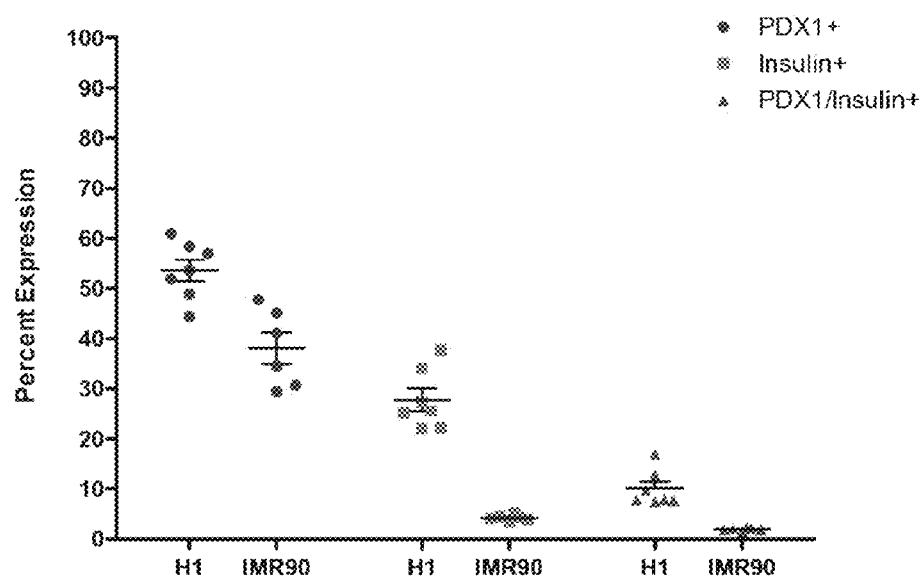
FIG. 18 shows that the present protocol is applicable to iPS cells to a lesser extent.

The protocol is effective in iPS cells. FIG. 18 is a graph that compares protein expression in H1 cells and an iPS cell line (IMR90). Other iPS lines can be differentiated effectively with this protocol (CD001, CD002).

Alterations at Stage 2

In a prior protocol we used bFGF (FGF2) during Stage 2. We next examined whether FGF2 would increase key endoderm markers compared to FGF7.

Figure 19:
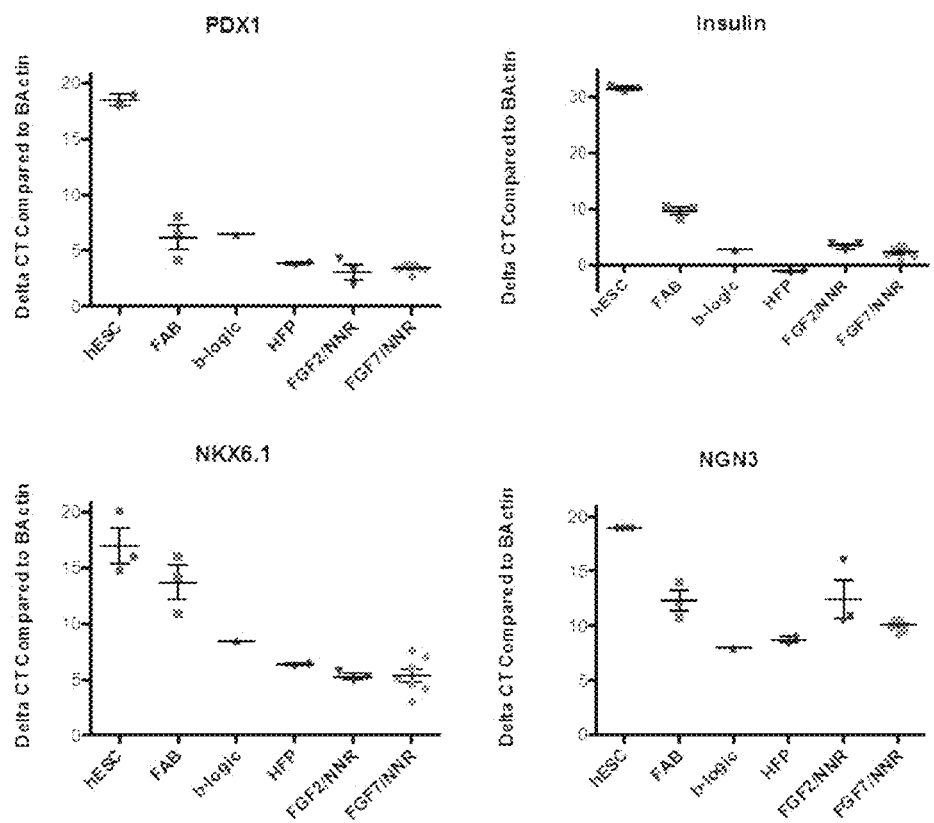
FIG. 19 shows that the alternations at Stage 2 of the present protocol do not alter gene expression.

First, alterations at Stage 2 do not alter gene expression. In FIG. 19, the gene expression is compared to undifferentiated cells collected at Day 0 and B-Actin is the internal control. On the y axis is delta CT (instead of fold change), thus, the lower the value the greater the gene expression. Similar gene expression was observed between cells treated with FGF2 or FGF7 during Stage 2.

Figure 20:
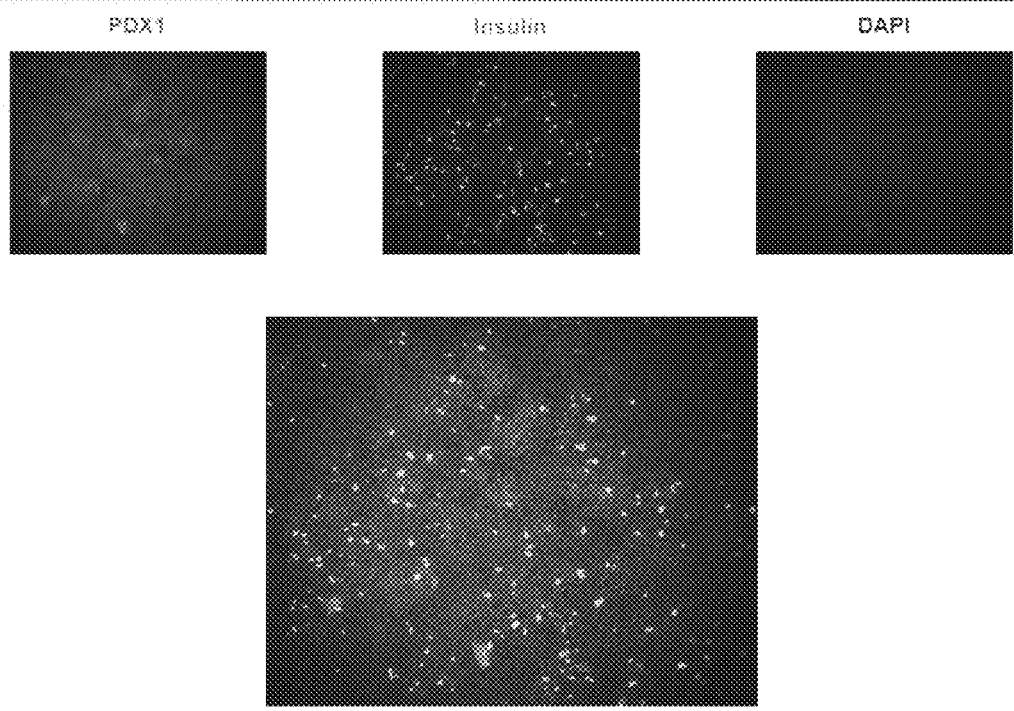
FIG. 20 shows that the alternations at Stage 2 decrease PDX1 and insulin protein expression.

Second, alterations at Stage 2 may decrease PDX1 and insulin protein expression. As shown in FIG. 20, interestingly, although gene expression was similar, there was less insulin protein expression when cells were treated with FGF2 at Stage 2. Therefore, we believe that FGF7 is a better choice.

Alterations at Stage 3 or 4

We also examined whether changes to Stage 3 (the addition or loss of nicotinamide) and changes to Stage 4 (the addition or loss of Noggin) altered gene and protein expression beneficially.

Figure 21:
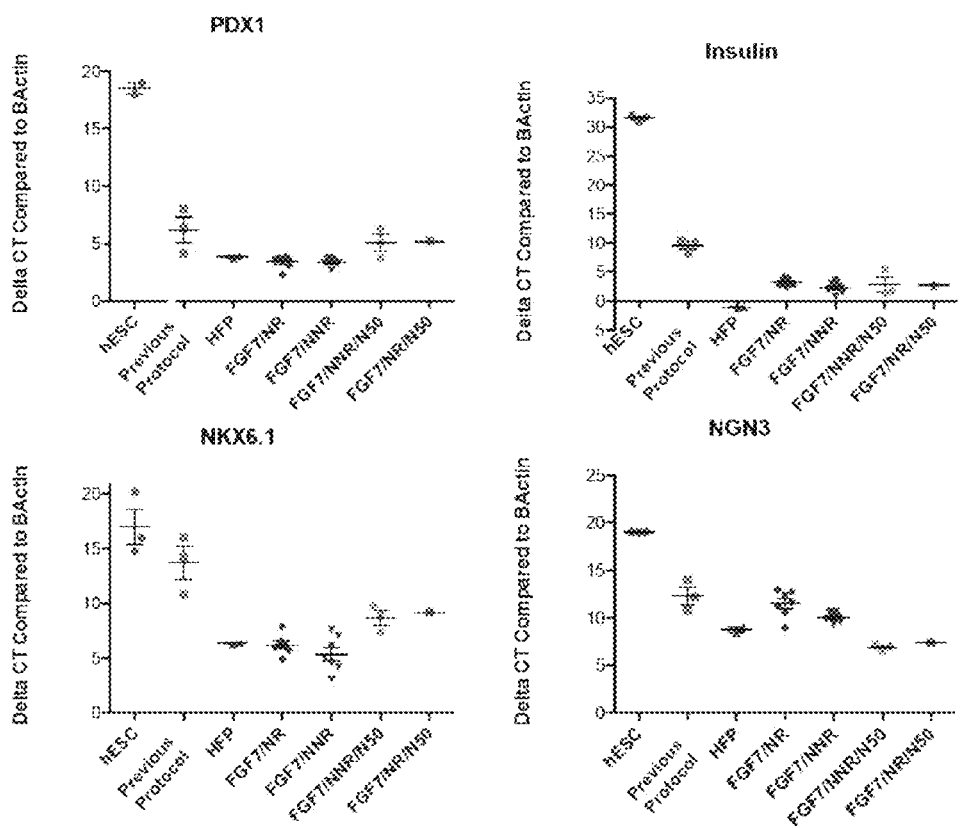
FIG. 21 shows that the alternations at Stage 3 and Stage 4 alter gene expression minimally.

First, alterations at Stage 3 and 4 altered gene expression minimally. As shown in FIG. 21, the gene expression is compared to undifferentiated cells collected at Day 0 and B-Actin is the internal control. On the y axis is delta CT (instead of fold change), thus, the lower the value the greater the gene expression. The presence or absence of nicotinamide at Stage 3 did not alter gene expression. In contrast the addition of Noggin at Stage 4, decreased PDX1 and NKX6.1 gene expression and increased Neurogenin 3 expression. There was no difference in insulin gene expression following the addition of Noggin to Stage 4.

Figure 22:
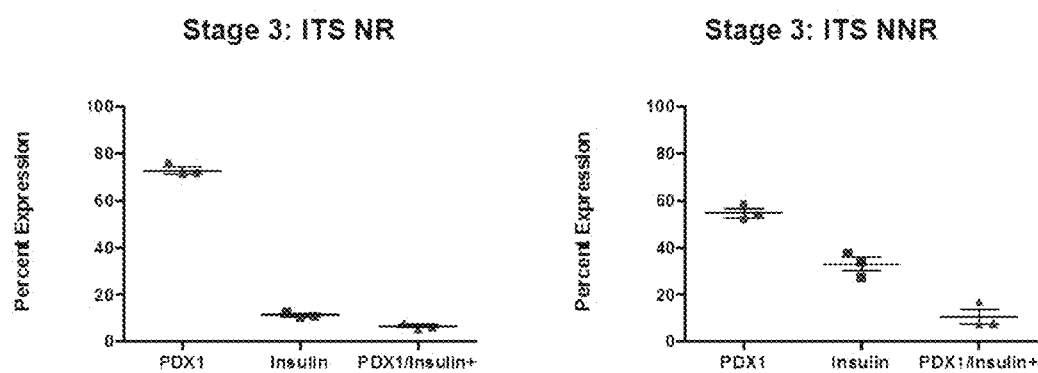
FIG. 22 shows that nicotinamide at Stage 3 significantly alters protein expression of PDX1 and insulin.

Second, nicotinamide alterations at Stage 3 significantly altered protein expression of PDX1 and insulin. To examine protein expression we collected cells at the end of Stage 4 and examined them by flow cytometry. As shown in FIG. 22, although there was no difference in gene expression, PDX1 protein expression is decreased and insulin protein expression is increased following the addition of nicotinamide. Interestingly, there is little difference in the double positive PDX and insulin positive cells.

Figure 23:
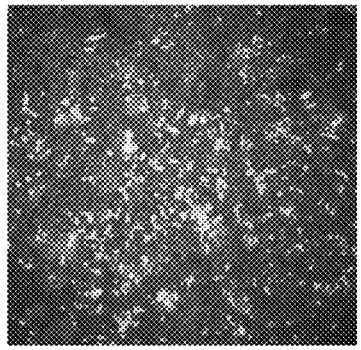
FIG. 23 shows that the alternations at Stage 3 and Stage 4 significantly alter protein expression of PD1 and insulin.
Figure 23:
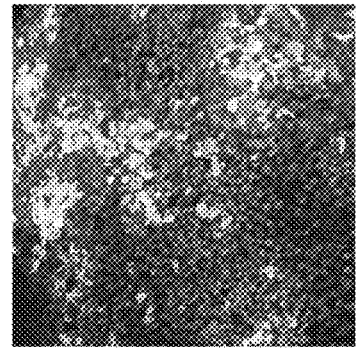
Figure 24:
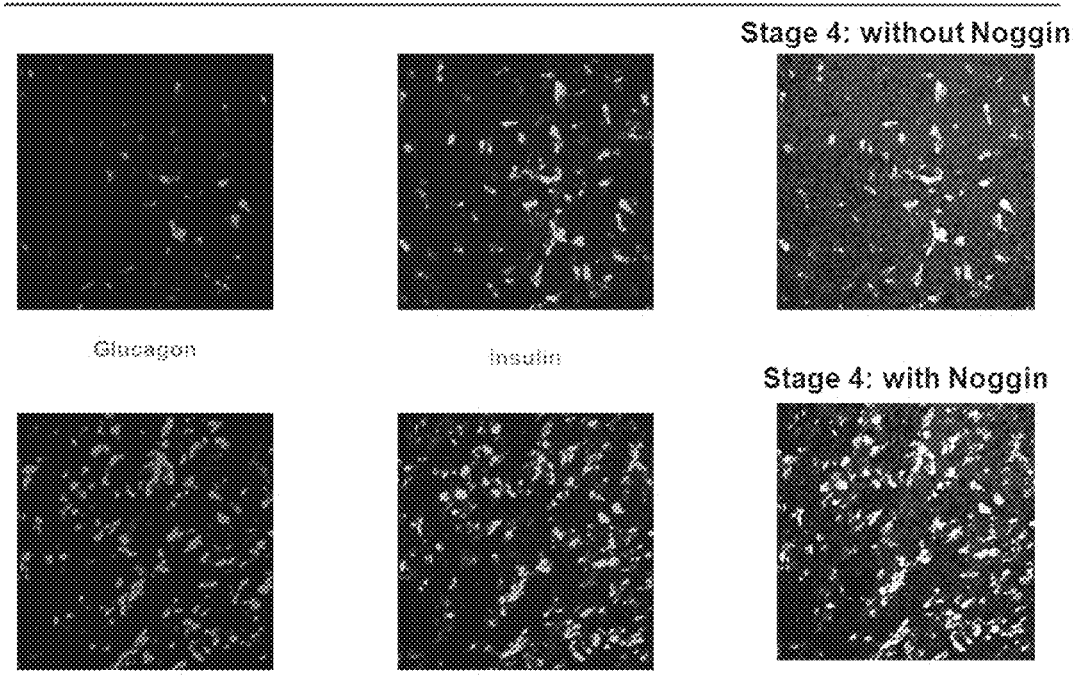
FIG. 24 are images showing the alternations at Stage 3 and Stage 4 significantly alter protein expression of PD1 and insulin.

Third, Noggin alterations at Stage 4 significantly altered protein expression. As shown in FIG. 23, examination by immunohistochemistry revealed while there was no difference in insulin gene expression there was increased clustering and insulin protein expression after the addition of Noggin at Stage 4. As shown in FIG. 24, even though there is increased insulin protein expression following the addition of Noggin a majority of those cells are still polyhormonal.

Evaluation of Necessary Factors for Stage 4

Figure 25:
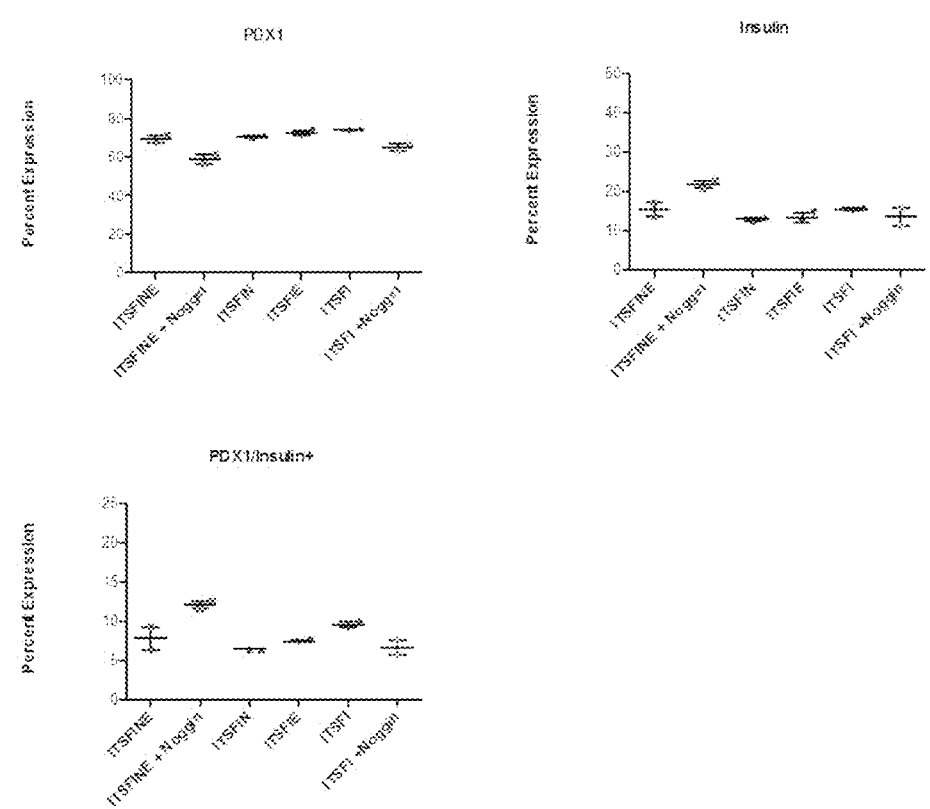
FIG. 25 shows the effects of the components of the cell culture medium on the expression levels of PDX1, insulin and PDX1/insulin$^+$.

As shown in the immunohistochemistry images in FIG. 23 and the quantitative flow cytometry data in FIG. 25, the addition of Noggin increases insulin expression. The loss of Exendin-4 results in little to no difference in protein expression of either PDX1 or insulin. The loss of nicotinamide also results in little to no loss in protein expression. However, the loss of both nicotinamide and Exendin-4 increases PDX1 and insulin double positive cells. Interestingly, the addition of Noggin in the absence of nicotinamide and Exendin-4 does not further increase the double positive cells and has little effect on increasing PDX1 and/or insulin protein expression over basal ITSFINE culture conditions. Additionally, whereas Noggin increases double positive cells in the context of ITSFINE, it has the opposite effect in the context of ITSFI media. Thus, the effect of Noggin is context dependent and synergistic with nicotinamide and Exendin-4.

We claim:

1. A method of culturing posterior foregut endoderm cells to produce cells of the pancreatic lineage, the method comprising the step of:

(a) culturing the posterior foregut endoderm cells for about 7 days in the presence of a serum free chemically defined medium (ITSFINE) comprising an effective amount of;
  i) insulin, transferrin, selenium, FGF7, islet neogenesis associated peptide (INGAP), nicotinamide, and exendin-4, and
  ii) Noggin,
wherein the cells are cultured on an extracellular matrix coated onto a membrane, and
wherein pancreatic lineage cells are produced, wherein the pancreatic lineage cells are insulin$^+$ cells.

2. A method of culturing human pluripotent stem cells to produce cells of the pancreatic lineage, the method comprising the steps of:
  (a) culturing human pluripotent stem cells for about 3 days in the presence of a chemically defined medium under conditions that induce formation of mesendoderm/primitive streak and definitive endoderm cells, wherein the medium comprises an effective amount of;
    i) fibroblast growth factor (FGF),
    ii) Activin A, and
    iii) bone morphogenetic protein (BMP);
  (b) culturing the cells from step (a) for about 3 days in the presence of a chemically defined medium comprising an effective amount of;
    i) insulin, transferrin, and selenium (ITS), and
    ii) fibroblast growth factor (FGF);
  (c) culturing the cells from step (b) for about 4 days in the presence of a chemically defined medium under conditions that induce formation of posterior foregut cells, wherein the medium comprises an effective amount of;
    i) insulin, transferrin, and selenium (ITS), and
    ii) Noggin-Nicotinamide-Retinoic acid (NNR); and
  (d) culturing the cells from step (c) for about 7 days in the presence of a serum free chemically defined medium (ITSFINE) comprising an effective amount of;
    i) insulin, transferrin, selenium, FGF7, islet neogenesis associated peptide (INGAP), nicotinamide, and exendin-4, and
    ii) Noggin,
  wherein the cells are cultured on an extracellular matrix coated onto a membrane, and
  wherein pancreatic lineage cells are produced, wherein the pancreatic lineage cells are insulin$^+$ cells.

3. The method of claim 2, wherein the stem cells are selected from the group consisting of human embryonic stem cells and human induced pluripotent stem cells.

4. The method of claim 2, wherein the extracellular matrix is selected from the group consisting of Matrigel™ and Laminin511.

5. The method of claim 4, wherein the extracellular matrix is Matrigel™.

6. The method of claim 2, wherein the membrane is a polycarbonate or polyester membrane.

7. The method of claim 6, wherein the polycarbonate or polyester membrane is Transwell™.

8. The method of claim 2, wherein in step (a) the effective amount of:
  i) FGF ranges from about 10 ng/ml to about 200 ng/ml,
  ii) Activin A ranges from about 10 ng/ml to about 200 ng/ml, and
  iii) BMP ranges from about 5 ng/ml to about 50 ng/ml.

9. The method of claim 8, wherein the FGF is selected from the group consisting of FGF2, FGF4, FGF7, FGF10 and the mixtures thereof.

10. The method of claim 8, wherein the BMP is selected from the group consisting of BMP2, BMP4, BMP7 and the mixtures thereof.

11. The method of claim 2, wherein in step (b) the FGF is selected from the group consisting of FGF2, FGF7 and the mixtures thereof.

12. The method of claim 2, wherein in step (b) the effective amount of FGF ranges from about 10-200 ng/ml.

13. The method of claim 2, wherein in step (c) the effective amount of NNR comprises;
  i) Nicotinamide at about 10 mM,
  ii) Noggin at from about 10 ng/ml to about 1000 ng/ml, and
  iii) Retinoic acid at about 100 nM to about 10 μM.

14. The method of claim 2, wherein in step (d) the effective amount of:
  i) FGF7 ranges from about 10 ng/ml to about 200 ng/ml,
  ii) Nicotinamide is about 10 mM,
  iii) Exendin-4 ranges from about 1 nM to about 100 nM, and
  iv) Noggin ranges from about 10 ng/ml to about 300 ng/ml.

15. The method of claim 2, wherein the pancreatic lineage cells co-express PDX-1, Nkx6.1, Ngn3, Sox9, and FoxA2.

16. The method of claim 2, wherein the pancreatic lineage insulin$^+$ cells comprise PDX1$^+$insulin$^+$ cells.

17. The method of claim 2, wherein the pancreatic lineage cells produce and process insulin endogenously and secrete C-peptide.

18. The method of claim 1, wherein the extracellular matrix is selected from the group consisting of Matrigel™ and Laminin511.

19. The method of claim 18, wherein the extracellular matrix is Matrigel™.

20. The method of claim 1, wherein the membrane is a polycarbonate or polyester membrane.

21. The method of claim 20, wherein the polycarbonate or polyester membrane is Transwell™.

* * * * *